United States Patent [19]
Arisawa et al.

[11] Patent Number: 6,143,541
[45] Date of Patent: *Nov. 7, 2000

[54] GENE ENCODING A PROTEIN HAVING SYMMETRIC HYDROLASE ACTIVITY FOR 4-SUBSTITUTED 1,4-DIHYDROPYRIDINE DERIVATIVES AND ITS EXPRESSION PRODUCT

[75] Inventors: Akira Arisawa, Yamato; Motoko Matsufuji, Komae; Takurou Tsuruta, Iwata; Kazuyuki Dobashi, Hadano; Takashi Nakashima, Fujisawa; Kunio Isshiki, Zama; Takeo Yoshioka, Ayase, all of Japan

[73] Assignee: Mercian Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/000,016

[22] PCT Filed: Jul. 30, 1996

[86] PCT No.: PCT/JP96/02147

§ 371 Date: Jan. 30, 1998

§ 102(e) Date: Jan. 30, 1998

[87] PCT Pub. No.: WO97/05243

PCT Pub. Date: Feb. 13, 1997

[30] Foreign Application Priority Data

Jul. 31, 1995 [JP] Japan ................................. 7-212975
Feb. 29, 1996 [JP] Japan ................................. 8-067478

[51] Int. Cl.[7] .............................. C12N 9/14; C12N 9/16; C12N 9/18; C12N 1/20; C12P 12/12
[52] U.S. Cl. ...................... 435/195; 435/196; 435/197; 435/122; 435/252.35; 435/320.1; 435/69.1; 536/23.1; 536/23.2
[58] Field of Search ................................. 435/195, 196, 435/197, 69.1, 320.1, 252.35, 122; 536/23.1, 23.2

[56] References Cited

U.S. PATENT DOCUMENTS 5,635,395 6/1997 Isshiki et al. .......................... 435/280

FOREIGN PATENT DOCUMENTS

94/05637 3/1994 WIPO.

OTHER PUBLICATIONS

Manome, T. et al., GenBank Database, Accession No. M20424, Jun. 1989.
Chem. Pharm. Bull., vol. 39, No. 1 (1991), pp. 108–111.
J. Med. Chem., vol. 29, No. 12 (1986), pp. 2504–2511.
Nucleic Acids Res., vol. 13, No. 24 (1985), pp. 8913–8926.
T. Shibanuma et al., "Synthesis of Optically Active 2–(N–Benzyl–N–methylamino)ethyl Methyl 2,6–Dimethyl–4–(m–nitrophenyl)–1,4–dihydropyridine–3,5–dicarboxylate (Nicardipine[1])", Chem. Phar. Bull., vol. 28, No. 9, pp. 2809–2812, (1980).
K. Achiwa et al., "Acyloxymethyl as an Activating Group in Lipase–Catalyzed Enantioselective Hydrolysis. A Versatile Approach to Chiral 4–Aryl–1,4–dihydro–2,6–dimethyl–3,5–pyridinedicarboxylates" Tetrahedron Letters, vol. 32, No. 41, pp. 5805–5808, (1991).
C. J. Shih et al., "A Chemoenzymatic Synthesis of Optically–Active Dihydropyridines", Tetrahedron Letters, vol. 32, No. 29, pp. 3465–3468, (1991).

*Primary Examiner*—Ponnathapu Achutamurthy
*Assistant Examiner*—Peter P. Tung
*Attorney, Agent, or Firm*—Wenderoth Lind & Ponack, L.L.P.

[57] ABSTRACT

This invention provides DNA fragments for efficiently preparing a protein having asymmetric hydrolase activity for 4-substituted 1,4-dihydropyridine derivatives, transformants obtained by using such a DNA fragment, and a process for preparing the aforesaid enzyme. Specifically, an isolated gene derived from the chromosome of *Streptomyces viridosporus* and encoding a protein having asymmetric hydrolase activity for 4-substituted 1,4-dihydropyridine derivatives, plasmids having the aforesaid gene integrated thereinto, transformants obtained by using such a plasmid, and a process for preparing the aforesaid enzyme by using such a transformant are disclosed. A process for the enzymatic conversion of 4-substituted 1,4-dihydropyridine derivatives by using the aforesaid enzyme is also disclosed.

5 Claims, 7 Drawing Sheets

Restriction map of dhpA dhpA: 0→2.94
mel : 3.24→4.07
tsr : 4.93→4.13

Lanes 1,5: Molecular weight markers.

Lane 2: The culture supernatant of A-914(pDE88)-5.

Lane 3: The ammonium sulfate precipitate (60-80% fraction) of A-914(pDE88)-5.

Lane 4: The A-914(pDE88)-5 fraction from a butyl-Toyopearl column.

Protease Activities of A-914 and Protease P6

Lipase Activities of A-914 and Lipase B

FIG. 11

```
DHP-A   205'  LDT---SVGQIGAPKAWSAGYDGKGVKIAVLDTGVDTSHPDLKGRVTASKNFTAAPG-AG
              .  *    *  .*.*  . *  .**.*******...*****.  *.  .  .*  .
Subtilisin 1" AQTVPYGIPLIKADKVQAQGFKGANVKVAVLDTGIQASHPDLN--VVGGASFVAGEAYNT 261'  DKVGHGTHVASIAAGTGAQSKGKYKGVAPGAAILNGKVLDDSGFGDDSGILAGMEWAAAQ
              * *******..*.. *     **.....*..*..*:.****.  .
         59"  DGNGHGTHVAGTVAALD-NTTGVL-GVAPSVSLYAVKVLNSSGSGTYSGIVSGIEWATTN 322'  GADVVNMSLGGMDTPETDPLEAAVDKLSAEKGVLFAIA--AGNEG-PESIGSPGSADAAL
              * .** .......           *  *    . *  ** *..*
        117"  GMDVINMSLGG--PSGSTAMKQAVDNAYARGVVVVAAAGNSGSSGNTNTIGYPAKYDSVI 378'  TVGAVDDKDKLADFSSTGPRLGDGAIKPDVTAPGVDITAASAEGNDIGQEVGEGPAGYMT
              .***.....**.*.       . *** .          .    ..   *  *
        175"  AVGAVDSNSNRASFSSVGAEL------EVMAPGAGVYSTYP-----------TSTYAT 438'  ISGTSMATPHVAGAAALLKQQHPDWTSAELKGALTGSTKGGKYTPFEQGSGRIQADKALQ
              .:***.**.****           .:.       .   *     *
        216"  LNGTSMASPHVAGAAALILSKHPNLSASQVRNRLSSTATYLGSS-FYYGKGLINVEAAAQ 274"

498'  QTVIADPVSVSFGVQQWPHTDDEPVTKQLTYRNLGTQDVTLKLTSTATDPKGKAAPAGFF

558'  TLGATTVTVPAGGSASVDMTADTRLGGTVDGAYSAYVVATGGGQTVRTAAAVQREVESYD

618'  VTVRHIGRDGKPTTEHLTDLIGYAGLGSGRGYGAPATDTATLRLPKGTYLVDSWIAKDFG

678'  TLKGGIDWLVQPKLSVTKDTTLTLDARTTKAADITVPDPKAKPLSATIGYTYDTAGI    734'
```

▼ ; Active site

GENE ENCODING A PROTEIN HAVING SYMMETRIC HYDROLASE ACTIVITY FOR 4-SUBSTITUTED 1,4-DIHYDROPYRIDINE DERIVATIVES AND ITS EXPRESSION PRODUCT

BACKGROUND OF THE INVENTION

1. Field of the Invention

This invention relates to proteins having asymmetric hydrolase activity for 4-substituted 1,4-dihydropyridine derivatives, genes encoding the proteins, and the use of the proteins.

2. Description of the Related Art

Of 4-substituted 1,4-dihydropyridine derivatives, those in which two different substituents are attached to the 3- and 5-positions of the dihydropyridine ring have an asymmetric carbon atom at the 4-position thereof and exist in the form of two optical isomers. As a result of investigations on the biological properties of these compounds, it has recently been reported that there is a difference in pharmacological activity, in vivo dynamic behavior, safety and other properties between the optical isomers of each compound [K. Tamazawa et al., J. Med. Chem., Vol. 29, 2504 (1986)]. Where such a compound having an asymmetric carbon atom is used as a drug, the conception of administering only one isomer favorable for use as a drug is being popularized so that no extra burden may be imposed on the living body. From this point of view, various processes for the preparation of optically active 3,5-disubstituted derivatives of 4-substituted 1,4-dihydropyridines are being investigated.

As a general method for the synthesis of optically active 4-substituted 1,4-dihydropyridine derivatives (in particular, 3,5-dicarboxylic acid monoesters), there is known a process comprising the steps of using a (4R)-1,4-dihydropyridine-3 or 5-carboxylic acid monoester as an intermediate and introducing a desired ester group thereinto [A. Ashimori et al., Chem. Pharm. Bull., Vol. 39, 108 (1991)]. Well-known methods for the preparation of such optically active intermediates [i.e., (4R)-1,4-dihydropyridine-3,5-carboxylic acid monoesters] include the chemical process of Shibanuma et. al. [Chem. Pharm. Bull., Vol. 28, 2809 (1980)], as well as the enzymatic process of Achiwa et al. [Tetrahedron Letters, Vol. 32, 5805 (1991)] and the enzymatic process of Charles J. Sih et al. [Tetrahedron Letters, Vol. 32, 3465 (1991)].

However, the above-described processes do not always make it possible to prepare the desired compounds efficiently. Consequently, the present inventors have proposed a simpler and efficient process for converting a 4-substituted 1,4-dihydropyridine-3,5-dicarboxylic acid diester to the corresponding 3,5-dicarboxylic acid monoester efficiently by using a culture of a microorganism such as bacteria of the genera Streptomyces, Paecilomyces, Botryodioplodia and Alternaria (see the pamphlet of PCT International Publication No. 94/05637).

However, there still exists a need for the provision of a more efficient means for the preparation of optically active 4-substituted 1,4-dihydropyridine-3,5-dicarboxylic acid monoesters.

Accordingly, an object of the present invention is to provide isolated genes which are conducive to the efficient preparation of the aforesaid optically active compounds, expression plasmids containing such genes, transformants obtained by using such plasmids, and proteins obtained by culturing such transformants and having asymmetric hydrolase activity for 4-substituted 1,4-dihydropyridine derivatives, as well as means associated with the use thereof.

SUMMARY OF THE INVENTION

The present inventors have succeeded in cloning a DNA fragment containing a gene encoding a protein having asymmetric hydrolase activity for 4-substituted 1,4-dihydropyridine derivatives (hereinafter referred to as "1,4-DHPDs"), from the chromosomal DNA of Streptomyces viridosporus belonging to the aforesaid genus Streptomyces, and expressing the aforesaid gene.

Moreover, as a result of the sequence determination of the aforesaid gene and the characterization of the protein obtained by the expression thereof, there has been obtained extensive information on the relationship between the primary structure of the protein and the aforesaid asymmetric hydrolase activity thereof, and the like. Furthermore, as a result of retrieval on sequence homology and the like by using a database including the amino acid sequences of the aforesaid protein and various other proteins, it has also been found that the protein of the present invention has a certain degree of amino acid sequence homology with subtilisin [see Jacobs, M. et al., Nucleic Acids Res. (1985), 13:8913–8926] and is presumed to have Asp, His and Ser as active sites.

Thus, according to the present invention, there is provided an isolated gene containing at least that portion of the amino acid sequence represented by SEQ ID NO:7 which extends from Asp(29) to Ser(238), and encoding a protein having asymmetric hydrolase activity for 1,4-DHPDs, or a DNA fragment hybridizable with the gene.

Moreover, the present invention also provides a plasmid constructed by integrating the aforesaid gene into a vector, a transformant obtained by using this plasmid, and a process for the preparation of a protein having asymmetric hydrolase activity for 1,4-DHPDs by culturing the aforesaid transformant.

Furthermore, the present invention also provides a process for the preparation of optically active (4R)-1,4-dihydro-2,6-dimethyl-4-(nitrophenyl)pyridine-3,5-dicarboxylic acid monoester derivatives which comprises bringing a protein having such enzyme activity into contact with a compound of the formula

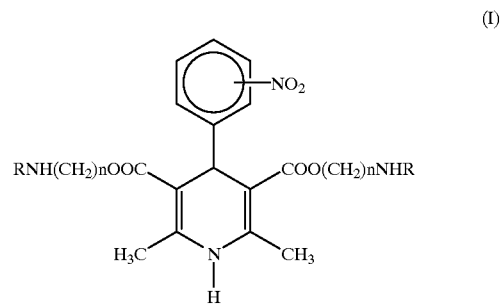

(I)

wherein R is a lower alkanoyl group, a heterocyclic carbonyl group, a halogen-substituted acetyl group, an alkoxyacetyl group, an aryloxyacetyl group, a substituted or unsubstituted phenyl-lower alkanoyl group, a phenyl-substituted or unsubstituted lower alkenoyl group, an alkoxy- or alkenyloxycarbonyl group, an aralkyloxycarbonyl group or organic sulfonyl group, and n is an integer of 2 to 4, or a salt thereof in an aqueous medium; and recovering an optically active 4-substituted 1,4-dihydropyridine compound of the formula

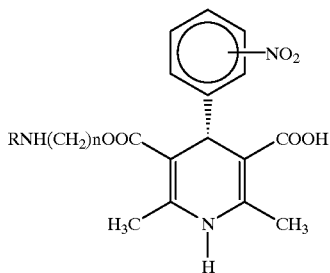

(II)

wherein R and n have the same meanings as described above, or a salt thereof.

Some of the aforesaid dicarboxylic acid monoester derivatives prepared in this manner are useful as intermediates for the synthesis of optically active 1,4-DHPDs which are well known per se and useful as prophylactic and therapeutic agents for ischemic heart diseases, hypertension and the like.

BRIEF DESCRIPTION OF THE DRAWINGS

FIG. 11 shows partial amino acid sequences expressed by the one-letter abbreviations for amino acids, indicating the degree of homology of the protein (DHP-A) of the present invention with subtilisin derived from *Bacillus linchenifornis* [Jacobs, M. et al.; Nucleic Acids Res. (1985), 13:8913–8926]. In FIG. 11, the arrows indicate active sites in the amino acid sequence of DHP-A, the asterisks indicate amino acids common to both sequences, and the dots indicate amino acids having an analogy between both sequences. The numeral 205' at the N-terminus and the numeral 734' at the C-terminus correspond to the respective amino acid numbers in SEQ ID NO:2 [i.e, Leu(205) and Ile(734)].

DESCRIPTION OF THE PREFERRED EMBODIMENTS

Figure 1:
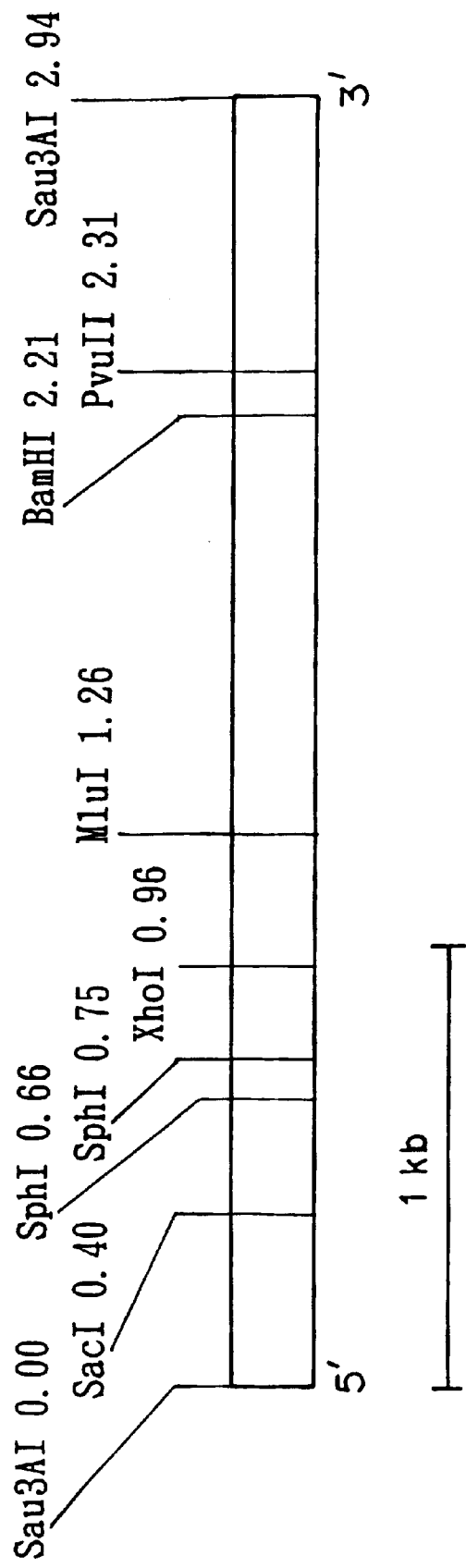
FIG. 1 is a restriction map of a DNA fragment derived from the chromosomal DNA of *Streptomyces viridosporus* and containing the gene (dhpA) encoding a protein (DHP-A) having asymmetric hydrolase activity for 1,4-DHPDs.

The three-letter abbreviations and one-letter abbreviations for amino acids used in the specification, sequence listing and drawings are based on the notation system commonly employed in the art.

Moreover, the expression "protein having asymmetric hydrolase activity for 4-substituted 1,4-dihydropyridine derivatives" as used herein denotes any protein having at least such activity that, when it is made to act on a substrate comprising a compound of the above formula (I), the substrate can be converted into a compound of the above formula (II).

The present inventors have found that the proteins having such activity are ones containing at least that portion of the amino acid sequence represented by SEQ ID NO:7 which extends from Asp(29) to Ser(238). (In the present specification and the claims, the numeral given in parentheses next to a symbol for an amino acid means a number indicating the location of the amino acid in the corresponding sequence.) This may be understood from the fact that, when the amino acid sequence of a protein in accordance with the present invention is compared with the amino acid sequence of subtilisin derived from *Bacillus lincheniformis* as shown in FIG. 11, the protein of the present invention is presumed to have, as active sites, aspartic acid (Asp) and histidine (His) residues in addition to a serine (Ser) residue and is considered to belong to be a member of the serine protease family.

Accordingly, the present invention first provides an isolated gene (or DNA fragment) containing, as an essential sequence, that portion of the amino acid sequence represented by SEQ ID NO:7 which extends from Asp(29) (i.e., an active site located on the N-terminal side) to Ser(238) (i.e., an active site located on the C-terminal side), and encoding a protein having asymmetric hydrolase activity for 1,4-DHPDs, or a DNA fragment hybridizable with the gene. Specific examples of the DNA fragment hybridizable with the gene include DNA fragments having a nucleotide sequence common to the gene in a definite part, and having several different nucleotide sequences at the 5' or 3' terminus or in an internal sequence. Such fragments can express and thereby produce proteins having the same enzyme activity as the protein produced by the corresponding gene, or can at least be used for the cloning of the aforesaid gene.

Typical examples of the aforesaid protein include a protein composed of 520 amino acid residues as represented by SEQ ID NO:7; and proteins obtained by removing some amino acid residues from the C-terminus of the aforesaid protein, such as a protein having the amino acid sequence extending from Leu(1) to Ser(518) of SEQ ID NO:7 and a protein having the amino acid sequence extending from Leu(1) to Pro(512) of SEQ ID NO:7. Moreover, proteins obtained by adding an amino acid sequence or sequences to the N-terminus and/or C-terminus of SEQ ID NO:7 also fall within the scope of the aforesaid protein, and specific examples thereof include a protein having the amino acid sequence obtained by adding "Ile Gly Tyr Thr Tyr Asp Thr Ala Gly Ile" [see Ile(725) to Ile(734) of SEQ ID NO:4] to the C-terminus of SEQ ID NO:7; and proteins having the amino acid sequences represented by SEQ ID NO:4 and SEQ ID NO:2. Specific examples of the genes encoding these proteins are ones having the DNA sequences represented by SEQ ID NO:1 and SEQ ID NO:3.

The aforesaid genes provided by the present invention may be used to produce proteins having asymmetric hydrolase activity for 1,4-DHPDs, by integrating each of them into a suitable expression vector to construct a recombinant plasmid and transforming a suitable host microorganism with the recombinant plasmid.

Accordingly, the present invention also provides a recombinant plasmid carrying a gene as described above. For this purpose, it is convenient to use an expression vector constructed so as to allow a foreign gene to be expressed stably. Useful expression vectors include, but are not limited to, pIJ680 and pIJ425 having a gene (aph or aphII) encoding aminoglycoside phosphotransferase [for the physical maps of these plasmids and the base sequence of aph, see D. A. Hopwood et al., Genetic Manipulation of Streptomyces—A Laboratory Manual, The John Innes Foundation (1985); and for the base sequence of aphII, see E. Beck et al., Gene, 19, 327–336 (1982)].

A typical technique for preparing a gene in accordance with the present invention by using such a vector plasmid in the present invention is briefly described below.

For example, the inserted fragment containing the gene (hereinafter referred to as "dphA") represented by SEQ ID NO:3 and encoding a protein having asymmetric hydrolase activity for 1,4-DHPDs is one obtained by partially digesting the chromosomal DNA of *Streptomyces viridosporus* with the restriction enzyme Sau3AI. Consequently, this gene is disintegrated in an attempt to excise it from the plasmid with Sau3AI. This problem may be solved, for example, by using a suitable primer to amplify the 2.54 kb SacI-Sau3AI (changed to BamHI) by PCR, inserting the amplified fragment into the BamHI site on the aph gene of pIJ680 or the SphI site on the aphII gene of pIJ425, and selecting a plasmid in which the direction of the inserted dhpA gene is opposite to the direction of the aph or aphII gene.

This plasmid yields a product comprising a dhpA-derived protein composed of 734 amino acids and having fused therewith a functionally insignificant protein composed of 29 amino acids (see SEQ ID NO:5) (pIJ680) or 15 amino acids (see SEQ ID NO:6) (pIJ425).

The aforesaid gene of the present invention can advantageously be prepared from *Streptomyces viridosporus* (for example, its A-914 strain which was deposited on Jul. 29, 1992 with the Research Institute of Microbiological Technology, the Agency of Industrial Science and Technology, then transferred to the international deposition department thereof under the provisions of the Budapest Treaty, and assigned an accession number of FERM BP-4334), though the source microorganism is not limited thereto. Moreover, this gene of the present invention is contained in an about 3.0 kb DNA fragment excised from the chromosome of the aforesaid strain with the restriction enzyme Sau3AI and represented by the restriction map of FIG. 1.

Accordingly, the term "isolated gene" as used herein comprehends not only the above-described DNA fragment, but also a DNA fragment comprising only the polynucleotide portion excised from the aforesaid fragment and encoding a protein having the desired enzyme activity, and a DNA fragment obtained by adding a foreign polynucleotide portion to the aforesaid fragment. In the latter case, if the sequence of the DNA fragment is determined as will be described later, it will be easy for those skilled in the art to identify and isolate the DNA fragment.

Thus, a DNA fragment containing the gene (dhpA) encoding a protein having asymmetric hydrolase activity for 1,4-DHPDs can readily be obtained from the aforesaid A-914 strain according to the genetic engineering techniques well known in the art. These techniques are taught in many laboratory manuals and any of them may be employed. However, since the A-914 strain is an actinomycete, it is desirable to refer to laboratory manuals describing gene engineering techniques for actinomycetes [for example, D. A. Hopwood et al., Genetic Manipulation of Streptomyces, A Laboratory Manual (1985) (John Innes Foundation)].

The procedure for obtaining a DNA fragment in accordance with the present invention is briefly described below. The particular techniques may be selected from the well-known techniques described in the aforementioned laboratory manual of Hopwood et al., unless otherwise indicated.

Cloning of the Gene

Total DNA is extracted from cells of the A-914 strain according to the SDS-phenol method. This DNA is partially digested with the restriction enzyme Sau3AI. Then, the resulting digestion product is subjected to 0.8% agarose gel electrophoresis and thereby fractionated into fractions having lengths suitable for integration into vectors. Using T4 DNA ligase, these fractionated DNA fragments are ligated to a vector plasmid capable of utilizing, as a cloning site, the BamHI, BglII or BclI site having the same cohesive ends as the Sau3AI cleavage site (e.g., pIJ702 capable of utilizing the BGlII cleavage site).

Of various hosts into which this vector can be introduced, one which does not contain a protein having asymmetric hydrolase activity for 1,4-DHPDs is transformed with the aforesaid DNA fragments [for example, when pIJ702 is used, *Streptomyces lividans* 66 (FERM BP-737) may be used as the host]. Thus, there are obtained a large number of transformants having plasmids into which randomly selected regions of the donor genomic DNA have been integrated. These individual transformants are measured for asymmetric hydrolase activity for 1,4-DHPDs. The specific method for the measurement of hydrolase activity will be described later.

Thus, a transformant capable of expressing a protein having the desired activity can be isolated from the aforesaid transformants. With consideration for its subsequent use, it is convenient that the DNA fragment containing the dhpA gene of the present invention are left in a state integrated in the plasmid possessed by the transformant. This plasmid may be obtained by culturing the transformant and isolating the plasmid according to the alkali-SDS method. The plasmid DNA thus obtained is cleaved with various restriction enzymes, and the cleavage sites are mapped by analyzing the lengths of the cleaved DNA fragments by agarose gel electrophoresis. On the basis of the results thus obtained, a restriction map of the DNA fragment integrated into the plasmid can be constructed. The restriction map so constructed is shown in FIG. 1.

Accordingly, if it is desired to know whether or not a DNA fragment containing the dhpA gene of the present invention has been obtained, this may be done by generating transformants with a plasmid having the DNA fragment integrated thereinto and measuring them for asymmetric hydrolase activity for 1,4-DHPDs and by comparing the restriction map of the DNA fragment with that of FIG. 1 or (in the case of sequence determination) the base sequence of the DNA fragment with that represented by SEQ ID NO:3.

If necessary, the DNA fragment thus obtained may further be shortened by treatment with a restriction enzyme or exonuclease. Then, the DNA fragment may be integrated into a vector selected from various expression vectors including the aforesaid vector; actinomycete vectors such as pIJ350, pIJ41, pIJ943 and pIJ922; and *Escherichia coli* vectors widely used in general gene manipulations, such as pUC18 and pUC19. Thus, there can be obtained a plasmid in accordance with the present invention.

By reference to the above-described procedure, those skilled in the art will be able to obtain any of the recombinant plasmids carrying the aforesaid genes of the present invention.

Generation of Transformants Having a Plasmid into which a DNA Fragment Containing dhpA is Integrated Plasmids in accordance with the present invention can be introduced into hosts capable of receiving them. No particular limitation is placed on the types of the vector and the host because they may be suitably selected from a wide variety of combinations of vectors and hosts capable of receiving them. However, as a particularly practical combination, it is desirable to use a vector comprising a high-copy plasmid of an actinomycete, typified by pIJ702 as described above, and a host comprising an actinomycete such as *Streptomyces lividans* 66, *Streptomyces viridosporus* A-914 or *Streptomyces clavus* N-1284. The reasons for this are that ① dhpA can be expressed on a high level and ② the introduced plasmid is retained with structural stability. Moreover, especially when *Streptomyces viridosporus* A-914 or *S. clavus* N-1284 is used as the host, the resulting transformants have additional advantages in that ③ since the host itself has the ability to produce an asymmetric hydrolase for 1,4-DHPDs, an enhanced enzyme activity can be expected in conjunction with the enzyme activity derived from the introduced plasmid and in that ④ they show little side reaction with the reaction substrate and the reaction product.

According to the present invention, there are also provided transformants obtained by transforming a host microorganism (for example, a bacterial strain selected from the group consisting of *Streptomyces viridosporus*, *Streptomyces lividans* and *Streptomyces clavus*) with a plasmid carrying any of aforesaid genes, including, for example, *Streptomyces viridosporus* A-914(pDE88)-5. The aforesaid A-914(pDE88)-5 strain was deposited on Jul. 10, 1995 with the Research Institute of Microbiological Technology, and assigned an accession number of FERM P-15037. Then, this strain was transferred to international deposition under the provisions of the Budapest Treaty, and assigned an accession number of FERM BP-5574.

When these transformants are cultured in a nutrient medium, they produce a protein having asymmetric hydrolase activity for 1,4-DHPDs. Consequently, the protein having the aforesaid enzyme activity can be obtained by recovering the protein having the desired enzyme activity from the resulting culture.

Accordingly, the present invention also provides a process for the preparation of a protein having asymmetric hydrolase activity for 1,4-DHPDs by using a transformant as described above.

Since the use of genes in accordance with the present invention permits the expression of the proteins encoded by those genes, the present invention also provides the above-described proteins. However, for example, the protein expressed by culturing the aforesaid A-914(pDE88)-5 strain (FERM BP-5574) undergoes processing during cultivation and is accumulated in the form of a shortened protein. Accordingly, the proteins in accordance with preferred embodiment of the present invention include a protein having the amino acid sequence represented by SEQ ID NO:7 [Leu(1) to Thr(520)]; proteins obtained by removing some amino acid residues from the C-terminus of the aforesaid protein [for example, a protein having the amino acid sequence extending from Leu(1) to Ser(518) and a protein having the amino acid sequence extending from Leu(1) to Pro(512)]; and a protein having the amino acid sequence obtained by adding "Ile Gly Tyr Thr Tyr Asp Thr Ala Gly Ile" [see Ile (725) to Ile (734) of SEQ ID NO:4] to Thr at the C-terminus of the aforesaid amino acid sequence extending from Leu(1) to Thr(520).

No particular limitation is placed on the aforesaid nutrient medium used for the preparation of the proteins in accordance with the present invention, and any common culture medium for the cultivation of microorganisms may be used. For example, there may be used any carbon sources that can be utilized by the aforesaid microorganisms. Specific examples thereof include sugars such as glucose, fructose, sucrose and dextrin; sugar alcohols such as glycerol and sorbitol; and organic acids such as fumaric acid and citric acid. Usually, these carbon sources are preferably added to the culture medium in an amount of about 0.1 to 10%.

Usable nitrogen sources include, for example, inorganic acid ammonium salts such as ammonium chloride, ammonium sulfate and ammonium phosphate; organic acid ammonium salts such as ammonium fumarate and ammonium citrate; and natural organic nitrogen sources such as meat extract, yeast extract, corn steep liquor and casein hydrolyzate. Of these nitrogen sources, organic nitrogen sources can also be used as carbon atoms in many cases. Usually, these nitrogen sources are suitably added in an amount of 0.1 to 10%.

Usable inorganic salts include, for example, alkali metal phosphates such as potassium phosphate and sodium phosphate; alkali metal chlorides such as potassium chloride and sodium chloride; and metallic sulfates such as magnesium sulfate and ferrous sulfate. These inorganic salts are suitably used in an amount of 0.001 to 1%.

Using the above-described culture medium, the microorganism (or transformant) may be cultured under aerobic conditions at a temperature of 20 to 40° C., preferably 28 to 37° C., and a pH of 5 to 9, preferably 6 to 8.

The protein having asymmetric hydrolase activity for 1,4-DHPDs, which has been prepared in the above-described manner, may be used in the form of an isolated protein, the culture itself, a crudely purified product of the culture, or an immobilized enzyme to prepare a compound of the above formula (II) by bringing the enzymatically active protein into contact with a compound of the above formula (I) in an aqueous medium. Accordingly, the present invention also provides a process for the enzymatic conversion of a compound of formula (I) to a compound of formula (II) by using the protein having asymmetric hydrolase activity for 1,4-DHPDs.

The aforesaid aqueous medium can be an aqueous solution which may be buffered, if necessary. The compound of formula (I) is dissolved in water or a cosolvent (e.g., acetone or dimethyl sulfoxide) and added to the aqueous medium. After this aqueous medium is adjusted to a pH of 7.0 to 9.5, the compound of formula (I) is reacted by contact with the aforesaid enzyme, usually at a temperature of 20 to 50° C. Thus, this compound can be converted to a compound of formula (II). After completion of the reaction, the aqueous medium is adjusted to a pH of 1.5 to 3.0 and then extracted with an organic solvent such as chloroform, ethyl acetate, butyl acetate or butanol. Moreover, if necessary, the product may be crystallized or purified by a suitable means such as redissolution or precipitation. Thus, the compound of formula (II) can be obtained in purified form.

The present invention is more specifically explained with reference to the following examples. However, it is to be understood that these examples are given merely to facilitate the understanding of the present invention.

EXAMPLE 1

Construction of the Plasmid pDE88

S. viridosporus A-914 strain (FERM BP-4334) was inoculated into 25 ml of TSB medium (Difco Tryptic Soy Broth 3.0%) and incubated with shaking at 28° C. for 3 days. 2 ml of the seed culture thus obtained was inoculated into 50 ml of YEME medium (34% saccharose, 0.3% Bacto Yeast Extract, 0.5% Bacto Pepton, 0.3% Bacto Malt Extract, 0.5% glycine, 5 mM $MgCl_2$, no pH adjustment) and incubated with shaking at 28° C. for 40 hours. This culture medium was centrifuged at 8000×g for 10 minutes to collect bacterial cells, and total DNA was extracted and purified therefrom according to the method described in the laboratory manual of Hopwood et al. [i.e., Genetic Manipulation of Streptomyces, John Innes Foundation (1985)].

80 µl of $H_2O$ 20 µl of tenfold concentrated M buffer [100 mM Tris-HCl (pH 7.5), 500 mM NaCl, 100 mM $MgCl_2$, 10 mM dithiothreitol] and 1 unit (0.25 µl) of the restriction enzyme Sau3AI were successively added to 100 µl of a solution containing 100 µg of the aforesaid DNA in TE [10 mM Tris-HCl (pH 8.0), 1 mM EDTA (pH 8.0)], and the resulting mixture was reacted at 37° C. for 30 minutes. Thereafter, the reaction mixture was extracted with an equal amount (200 µl) of a TE-saturated phenol-chloroform mixture [prepared by adding 0.2% of 8-quinolinol to phenol-chloroform-isoamyl alcohol (25:25:1)]. The aqueous layer was separated and further extracted with an equal amount of chloroform. The aqueous layer was separated, and 1/10 volume of 3 M sodium acetate and 3 volumes of ethanol were successively added thereto. After intimate blending, this mixture was cooled at −18° C. for 15 minutes and then centrifuged at 5000×g for 5 minutes to precipitate DNA. This DNA was washed once with 1 ml of 70% ethanol and dried under reduced pressure. The resulting residue was dissolved in 100 µl of TE.

After 11 µl of a tenfold concentrated gel loading buffer (25% Ficoll, 0.25% Bromophenol Blue) was added, the aforesaid solution was pipetted into four wells of 13 cm×13 cm 0.8% agarose gel and electrophoresed at 30 V by using the HindIII digestion product of λ phage DNA as a size marker. After electrophoresis, a gel part containing DNA corresponding to 4–6 kb was cut out, and the DNA was recovered and purified by using an Ultrafree C3 Unit 0.45 µm (manufactured by Nihon Millipore Ltd.). 1 µl of a previously dephosphorylated, BglII-linearized pIJ702 DNA solution (having a concentration of 1 µg/µl) was added to 9 µl of the resulting DNA solution (having a concentration of 0.5 µg/µl), and this vector-insert mixture was subjected to a ligation reaction (at 16° C. for 3 hours) by using a Ligation Kit ver. 1 (manufactured by Takara Shuzo Co., Ltd.).

The dephosphorylated BglII-linearized DNA solution of the vector pIJ702 was prepared as follows: 25 units (2.5 µl) of BglII was added to a total volume of 50 µl of a reaction solution [10 mM Tris-HCl (pH7.5), 100 mM NaCl, 10 mM $MgCl_2$, 1 mM dithiothreitol] containing 10 µg of pIJ702 DNA. This mixture was reacted at 37° C. for 4 hours and successively subjected to the above-described treatments including extraction with a phenol-chloroform mixture and with chloroform, precipitation with ethanol, washing with 70% ethanol, and drying. The resulting DNA was dissolved in 45 µl of 10 mM Tris-HCl (pH 8.0). To this solution were added 5 µl of a tenfold concentrated alkaline phosphatase buffer [500 mM Tris-HCl (pH 8.0), 1 mM EDTA] and 1 µl (1.7 units) of calf intestinal alkaline phosphatase (manufactured by Toyobo Co., Ltd.). This mixture was incubated at 37° C. for 1 hour and then incubated at 65° C. for 45 minutes to inactivate the enzyme. Thereafter, employing the same conditions as described above, this mixture was subjected to a series of treatments including extraction with a phenol-chloroform mixture and with chloroform, precipitation with ethanol, washing, and drying. By dissolving the resulting DNA in 10 µl of TE, a dephosphorylated BglII-linearized pIJ702 DNA solution was finally obtained.

After ligation, protoplasts (1×10⁹ cells) of S. lividans 66 were transformed with 15 µL of the reaction solution according to the method described in the aforementioned laboratory manual of Hopwood et al. For the purpose of selection with an antibiotic, 50 µg/ml of thiopeptin was used. When a donor DNA is inserted into a cloning site (BglII) located in the mel gene (melanin-producing gene) present in pIJ702, the mel gene is inactivated. When transformed strains have such a plasmid, they can readily be distinguished visually as strains not producing a black pigment (melanin). Colonies of non-melanin-producing strains were inoculated on DHP medium (3% TSB, 1.5% Bacto Agar, 500 µl/ml M-801) in the form of patches at a density of 25 strains per 8 cm plate, and incubated at 28° C. for 5 days. Using a cork borer (having an inner diameter of 6 mm), pieces of the culture medium having bacterial cells thereon were cut out, placed on several lanes of a silica gel TLC plate (formed by cutting therein 1 mm wide longitudinal slits at intervals of 8 mm), allowed to stand at room temperature for 30 minutes so as to cause the contents of the culture medium to diffuse out, and then dried. This plate was developed with a solvent system comprising chloroform-methanol (6:1). Thus, each lane was examined for the presence of the asymmetric hydrolysis product M-802 (with an Rf value of 0.53) of M-801 (with an Rf value of 0.59) in the culture medium.

Figure 2:
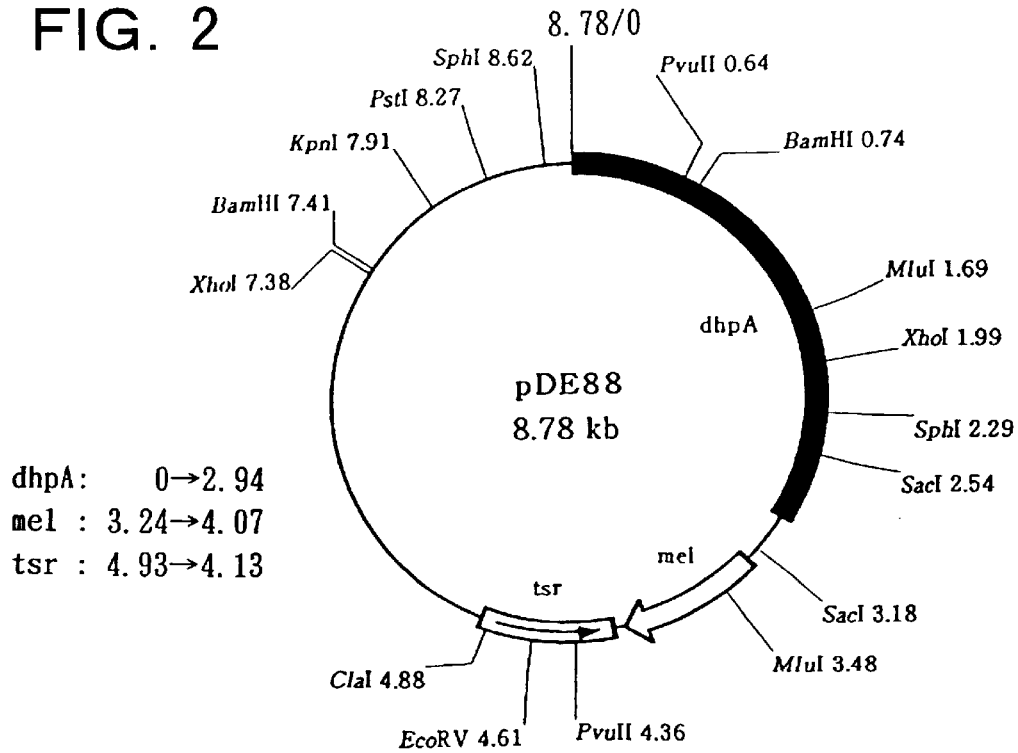
FIG. 2 is a diagram showing the structure of the plasmid pDE88 carrying the gene of the present invention.

Thus, a strain having asymmetric hydrolase activity for M-801, S. lividans (pDE88), was isolated from the transformants. In order to confirm that the desired gene (dhpA) had been cloned into the plasmid (named pDE88) possessed by this strain, pDE88 DNA was extracted and purified according to the well-known method described in the aforementioned laboratory manual of Hopwood et al., and S. lividans 66 was transformed therewith again to obtain a secondary transformed strain. As a result of TLC assays as described above, this strain exhibited asymmetric hydrolase activity for 1,4-DHPDs similarly to the initially obtained strain, revealing that pDE88 contained dhpA. pDE88 was cleaved with various restriction enzymes, and the lengths of the resulting fragments were analyzed by agarose gel electrophoresis. This revealed that a donor DNA fragment containing the about 3.0 kb dhpA gene shown in the restriction map of FIG. 1 had been integrated into the vector pIJ702. A diagram showing the structure of pDE88 is given in FIG. 2.

EXAMPLE 2

Generation of Transformants and Measurement of Enzyme Activity

Protoplasts were prepared from the actinomycete S. clavus N-1284 according to the usual method described in the aforementioned laboratory manual of Hopwood et al. Protoplasts were also prepared from S. viridosporus A-914 in the same manner as described above, except that TSB medium having 0.5% glycine and 5 mM $MgCl_2$ added thereto was used as the culture medium in place of YEME medium. For each type of protoplasts, 1 ml of a suspension containing 1×10⁹ cells was placed in a sterilized polystyrene tube (having a capacity of 15 ml; manufactured by Corning Glass Works) and centrifuged (5000×g, 10 minutes). After the supernatant was decanted, 10 μl of the plasmid pDE88 DNA solution (having a concentration of 1 μg/ml) obtained in Example 1 was added to the remaining protoplasts, followed by intimate mixing. After 0.4 ml of T buffer [a solution obtained by dissolving 1 g of polyethylene glycol (having a degree of polymerization of 1,000) in 3 ml of a solution containing 0.24% saccharose, 0.2% trace element solution[1] (described below), 0.023% $K_2SO_4$, 1.5% $CaCl_2$ and 50 mM Tris-maleic acid (pH 8.0)] was added thereto and the resulting mixture was allowed to stand at room temperature for 30 seconds, the protoplasts were washed with 10 ml of P buffer[2] (described below) and then inoculated on five plates of R3 medium (prepared by autoclaving a solution containing 13.5% saccharose, 0.05% KCl, 0.6% $MgCl_2.6H_2O$, 1% glucose, 0.4% Bacto Pepton, 0.4% yeast extract, 0.57% TEST and 2.2% Bacto Agar and adding thereto 1/100 volume of 0.5% $KH_2PO_4$, 0.3/100 volume of 5 M $CaCl_2$, and 1.8/100 volume of 1 N NaOH). After these plates were incubated at 28° C. for 16 hours, 2 ml of SNA medium (0.8% nutrient broth, 0.3% Bacto Agar) having 250 μg/ml (final concentration) of thiopentin added thereto was uniformly layered over each of the plates, and the incubation was continued for an additional 5 days.

| Trace element solution[1] (per liter): | |
|---|---|
| $ZnCl_2$ | 40 mg |
| $FeCl_3.6H_2O$ | 200 mg |
| $CuCl_2.2H_2O$ | 10 mg |
| $MgCl_2.4H_2O$ | 10 mg |
| $Na_2B_4O_7.10H_2O$ | 10 mg |
| $(NH_4)_6Mo_7O_{24}.4H_2O$ | 10 mg |
| P buffer[2]: | |
| 10.3% | Saccharose |
| 0.025% | $K_2SO_4$ |
| 0.202% | $MgCl_2.6H_2O$ |
| 0.2%(v/v) | Trace element solution |
| (after autoclaving) | |
| 0.005% | $KH_2PO_4$ |
| 0.368% | $CaCl_2.2H_2O$ |
| 0.573% | TES (pH 7.2) |

Consequently, 31 transformed strains were obtained when S. clavus N-1284 was used as the host, and 24 transformed strains were obtained when S. viridosporus A-914 was used as the host. Two strains derived from different hosts were selected and named S. clavus N-1284(pDE88)-6 and S. viridosporus A-914(pDE88)-5. Each of these strains, S. lividans (pDE88) and the strains used as hosts was cultured in 25 ml of TSB medium (to which 5 μg/ml of thiopentin was added in the case of transformed strains) for 4 days. 1 ml of the resulting culture, which was used as a seed culture, was added to 30 ml of C medium [2% glucose, 2% soluble starch, 2% Esusan Meat (soy-bean meal; manufactured by Ajinomoto Co., Inc.), 0.5% yeast extract, 0.25% NaCl, 0.32% $CaCO_3$, 0.0005% $FeSO_4$, 0.0005% $MnSO_4$, 0.0005% $ZnSO_4$, pH 7.4] and incubated with shaking at 28° C. for a period of time required to produce the maximum amount of a protein having asymmetric hydrolase activity for 1,4-DHPDs. This period of time was 3 days for S. lividans and S. lividans (pDE88), 4 days for S. clavus N-1284 and S. clavus N-1284(pDE88)-6, and 6 days for S. viridosporus A-914 and S. viridosporus A-914(pDE88)-5. Then, according to the method which will be described later, the resulting culture medium was measured for the specific activity of asymmetric hydrolase for 1,4-DHPDs. The results thus obtained are shown in Table 1.

Moreover, protease P6 (manufactured by Amano Pharmaceutical Co., Ltd.) known to have the ability to hydrolyze 1,4-DHPDs asymmetrically [T. Adachi et al., Tetrahedron Asymmetry, Vol. 4, 2061 (1933)] was used as a control enzyme and its enzyme activity was measured at the same time.

TABLE 1

| Transforming plasmid | Degree of conversion of M-801 to M-802 (mole %) [expressed in terms of protease P6 (mg/ml)] | |
|---|---|---|
| Host | None | pDE88 |
| S. clavus N-1284 | 12.4(1.2) | 43.4(5.2) |
| S. viridosporus A-914 | 23.0(2.3) | 74.5(10.4) |
| S. lividans TK24 | 0(0) | 53.8(6.8) |

(Note)

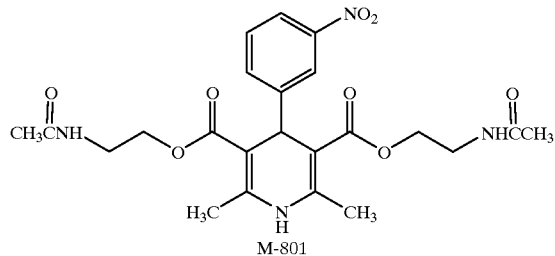

As can be seen from Table 1, S. clavus N-1284 and S. viridosporus A-914 are strains inherently exhibiting asymmetric hydrolase activity for 1,4-DHPDs. However, when they were transformed with pDE88, the enzyme activities (expressed in terms of protease P6) of the culture media thereof were increased by a factor of 4 or greater as compared with those of the respective hosts. On the other hand, although S. lividans is a strain inherently exhibiting no enzyme activity, a specific activity of 6.8 mg/ml as expressed in terms of protease P6 was detected in the culture medium of S. lividans (pDE88)-1 which is a transformant thereof. This activity was 5.6 times that of S. clavus N-1284 and 2.9 times that of S. viridosporus. The highest specific activity was exhibited by S. viridosporus A-914(pDE88)-5 and corresponded to 1.4 mg/ml as expressed in terms of protease P6. Thus, it has been revealed that all of the strains transformed with a plasmid containing the dhpA gene of the present invention secrete a large amount of an enzymatically active protein into the culture medium.

Activity Measuring Method

The enzyme activity was measured by reacting a test sample with M-801 used as a substrate and determining the asymmetric hydrolysis product M-802 by high-performance liquid chromatography (HPLC). Specifically, 0.1 ml of 0.5 M Tris-HCl buffer (pH 8.5), 0.2 ml of distilled water, 0.1 ml of a 5 M NaCl solution, 0.1 ml of a protein solution having asymmetric hydrolase activity for 1,4-DHPDs, and 5 μl of a dimethyl sulfoxide solution containing 30 mg/ml of M-801 were successively mixed together, and the resulting mixture was incubated at 40° C. for 1 hour. After 1 hour, the reaction was stopped by adding 0.1 ml of the reaction mixture to 2.4 ml of a solution composed of 0.02 M $KH_2PO_4$ and methanol in a ratio of 1:1. This solution was centrifuged at 8000×g for 10 minutes and the supernatant was measured for M-802 by HPLC. The operating conditions of HPLC were as follows: The column comprised YMC-A-302 [4.6 mm (I.D.)×150 mm], the mobile phase comprised a 0.02 M $KH_2PO_4$-methanol (1:1) solution, the flow rate was 0.8 ml/min., the ultraviolet wavelength of the detector was 350 nm, the temperature was 50° C., and the amount of test sample injected was 10 μl. Under these conditions, the retention times of M-801 and M-802 were 6–7 minutes and 4–5 minutes, respectively.

EXAMPLE 3

Culture of *S. viridosporus* A-914(pDE88)-5 and Ammonium Sulfate Fractionation

*S. viridosporus* A-914(pDE88)-5 was inoculated into 30 ml of C medium having 5 μg/ml of thiopeptin added thereto, and incubated with shaking at 28° C. for 4 days. The resulting culture was filtered to collect the supernatant. (The following operations were carried out at 4° C.) Ammonium sulfate was added to the supernatant so as to achieve 60% saturation. After 3 hours' stirring, this mixture was centrifuged at 9000×g for 20 minutes and the supernatant was separated. Then, ammonium sulfate was added to the supernatant so as to achieve 80% saturation, followed by stirring for 18 hours. After this mixture was centrifuged at 9000×g for 20 minutes, the precipitate was separated and dissolved in distilled water. This solution was regarded as a 60–80% ammonium sulfate fraction and subjected to the following purification procedure.

EXAMPLE 4

Purification of an Enzymatically Active Protein 20 ml of the aforesaid 60–80% ammonium sulfate fraction was applied at a flow rate of 34 ml/hr. to a column (26 mm×27.5 cm) of butyl-Toyopearl 650 (trade name; manufactured by Tosoh Corp.) which had been equilibrated with 50 mM Tris-HCl buffer (pH 7.5) containing 1.8 M ammonium sulfate. 100 ml each of 50 mM Tris-HCl buffer (pH 7.5) containing 1.8 M ammonium sulfate and 50 mM Tris-HCl buffer (pH 7.5) containing 0.4 M ammonium sulfate were used to create a linear concentration gradient extending from 1.8 M to 0.4 M ammonium sulfate. During elution, 10 ml fractions were collected and each of them was measured for asymmetric hydrolase activity for 1,4-DHPDs according to the activity measuring method described in Example 2. The fractions exhibiting the asymmetric hydrolase activity were combined to obtain a fraction of a protein having asymmetric hydrolase activity for 1,4-DHPDs (hereinafter referred to as DHP-A).

EXAMPLE 5

Measurement of Molecular Weight

Figure 3:
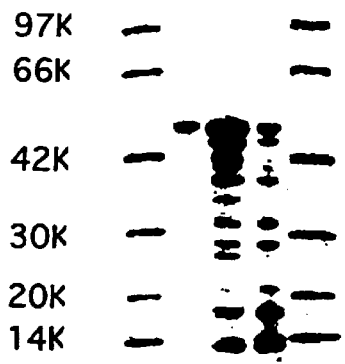
FIG. 3 is a view showing the results of SDS-PAGE (sodium dodecyl sulfate-polyacrylamide gel electrophoresis) performed to determine the molecular weight of a protein (DHP-A) having asymmetric hydrolase activity for 1,4-DHPDs in accordance with the present invention.

In order to determine the molecular weight of DHP-A, the aforesaid DHP-A fraction was subjected to SDS-PAGE (4–20% gradient) according to the method of Laemmli et al. [Nature, 227, 680–685 (1970)]. (The results thus obtained are shown in FIG. 3.) In FIG. 3, lane 1 shows molecular weight markers; lane 4, the culture supernatant of *S. viridosporus* A-914(pDE88)-5; lane 3, the 60–80% ammonium sulfate fraction of the same culture; and lane 2, the DHP-A fraction of A-914. From these results, the molecular weight of DHP-A was estimated to be about 55 kDa.

EXAMPLE 6

Measurement of Specific Activities

The activities of protease P6 and DHP-A were measured according to the activity measuring method described in Example 2. Moreover, the enzyme proteins were determined by using a protein assay kit (manufactured by Bio-Rad Co.) and their specific activities were calculated. The amount of enzyme which produces 1 mg of M-802 in an hour was taken as 1 U. As a result, DHP-A exhibited a specific activity equal to 2.12 times that of protease P6.

Measurement of Protease Activity

Figure 4:
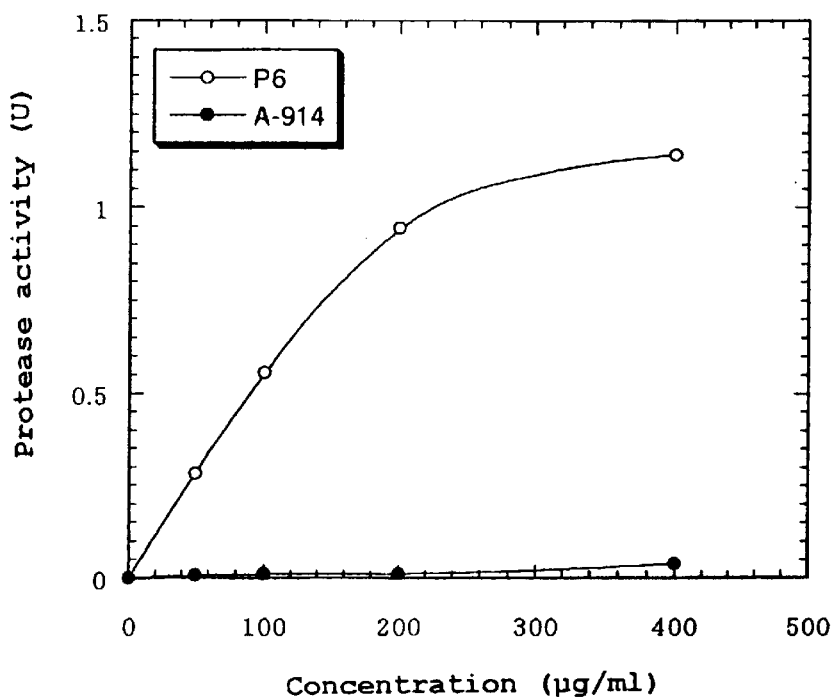
FIG. 4 is a graph showing the protease activity of the aforesaid protein (DHP-A) of the present invention in comparison with that of protease P6.

The protease activities of DHP-A and protease P6 were measured according to the ultraviolet absorption method. Specifically, a substrate solution was prepared by adding 10 ml of a 0.1 N sodium hydroxide solution, 30 ml of distilled water, and 40 ml of 0.05 M Tris-HCl buffer (pH 8.5) to 0.6 g of Hammarsten casein, adjusting the resulting solution to pH 8.5, and making up to 100 ml with distilled water. Enzyme solutions were prepared by adding 150 μl of a 2 mM calcium acetate solution to 50 μl each of protease P6 or DHP-A solutions having various concentrations. 1.0 ml of the substrate solution was added to 0.2 ml of each enzyme solution and incubated at 30° C. for 10 minutes. Thereafter, the reaction was stopped by adding 1.0 ml of a mixed trichloroacetic acid solution (i.e., a mixture composed of 1.8% of trichloroacetic acid, 22% of a 1 M sodium acetate solution, and 33% of a 1 M acetic acid solution). The reaction mixture was centrifuged at 8000×g for 5 minutes, and the absorbance of the supernatant was measured at 275 nm. The amount of enzyme which gives an absorbance of 1.0 at 275 nm as a result of reaction at 30° C. for 10 minutes was taken as 1 U. The results thus obtained are shown in FIG. 4. The protease activity of DHP-A was less than 1/30 of that of protease P6.

Measurement of Lipase Activity

Figure 5:
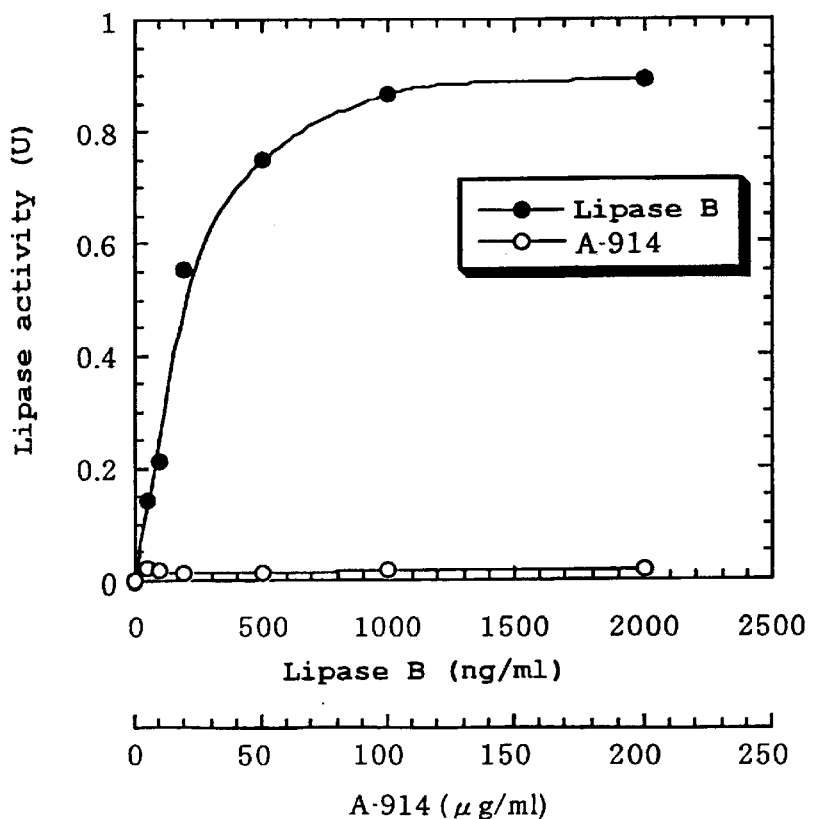
FIG. 5 is a graph showing the lipase activity of the aforesaid protein (DHP-A) of the present invention in comparison with that of lipase B.

The lipase activities of DHP-A and lipase B were measured by using a Lipase UV Autotest Wako (manufactured by Wako Pure Chemical Industries Ltd.). The amount of protein which gives an absorbance of 1.0 at 340 nm as a result of reaction at 37° C. for 6 minutes was taken as 1 U. The results thus obtained are shown in FIG. 5. No lipase activity was observed for DHP-A.

As described above, the protein DHP-A of the present invention, which has asymmetric hydrolase activity for 1,4-DHPDs, exhibits little protease (casein hydrolysis) activity or lipase activity, as contrasted with conventional enzymes used for the same purpose, such as protease P6 and lipase B. Accordingly, DHP-A is a novel protein having a unique enzyme activity and distinguishable from the aforesaid enzymes. Especially when compared with protease P6, DHP-A has the advantage of exhibiting a higher specific activity and more excellent thermal stability. Thus, it is a unique feature of the present invention that the protein having asymmetric hydrolase activity for 1,4-DHPDs exhibits little protease activity, and this means that the protein scarcely undergoes an autolytic reaction which is a cause of a reduction in the activity of protease P6.

Figure 6:
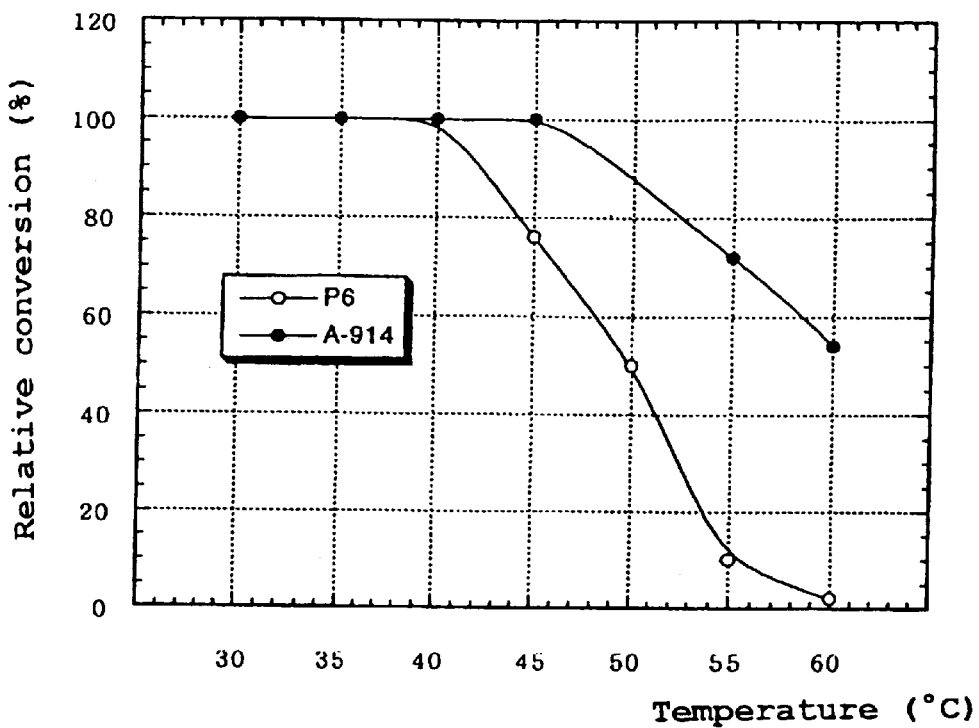
FIG. 6 is a graph showing the thermal stability of the aforesaid protein (DHP-A) of the present invention in comparison with that of protease P6.

Thermal Stability of Enzymatically Active Proteins 0.6 ml samples of a 1 mg/ml DHP-A solution or a 2 mg/ml protease P6 solution were mixed with 0.2 ml of 0.5 M Tris-HCl buffer (pH 8.5) and 0.2 ml of distilled water, and heat-treated at 30, 35, 40, 45, 50, 55 or 60° C. for 15 minutes. After the addition of a 30 ml/ml M-801 solution, the resulting mixtures were incubated for 60 minutes. These mixtures were measured for enzyme activity according to the activity measuring method described in Example 2. The results thus obtained are shown in FIG. 6. While DHP-A retained its approximately full activity over a temperature range of 30 to 45° C., the activity of protease P6 was reduced by about 25% at 45° C.

EXAMPLE 7

Determination of an N-terminal Amino Acid Sequence

Using a centrifugal filter tube having a fractionation molecular weight of 10,000 (Ultrafree C3LGC; manufactured by Nihon Millipore Ltd.), the enzyme solution purified in Example 4 was desalted and concentrated to obtain a solution having a concentration of 2 mg/ml. Then, 2.5 µl of this enzyme solution was applied to Phast Gel Homogeneous 12.5 (manufactured by Pharmacia Co.), placed in a Phast System (manufactured by Pharmacia Co.), and subjected to SDS-PAGE at 250 V and 10 mA for 1 hour. Thereafter, using a Phast Transfer (manufactured by Pharmacia Co.), the enzyme protein was transferred to a PVDF (polyvinyl difluoride) film (manufactured by Nihon Millipore Ltd.) by treatment at 20 V and 25 mA for 40 minutes. The transfer buffer used for this purpose comprised 25 mM Tris, 192 mM glycine (pH 8.3) and 20% methanol. After transfer, the film was air-dried. The part to which the enzyme protein had been transferred was cut out and subjected to N-terminal sequence analysis in a Model PSQ-1 Protein Sequencer (manufactured by Shimadzu Corp.), so that a sequence consisting of Leu-Asp-Thr-Ser-Val-Gly was determined. This sequence agreed with that portion of the amino acid sequence represented by SEQ ID NO:4 which extended from the 205th to the 210th amino acid. This revealed that the protein (DHP-A) having asymmetric hydrolase activity for 1,4-DHPDs, which was obtained in Example 4, had been undergone processing at its N-terminus and started from the 205th amino acid comprising leucine.

EXAMPLE 8

Determination of the C-terminal Amino Acid by Mass Spectrometry

Using a centrifugal filter tube having a fractionation molecular weight of 10,000 (Ultrafree C3LGC; manufactured by Nihon Millipore Ltd.), the enzyme solution purified in Example 4 was replaced by a 0.1% formic acid solution, and further desalted and concentrated to obtain a solution having a concentration of 2 mg/ml. Then, using 200 µl of this solution as a sample, the molecular weight of the enzyme protein was measured in the positive ion mode with a high-performance quadrupole triplex mass spectrometer (API III; manufactured by Perkin Elmer Siciex Co.). As a result, $[M+H]^+$ (in which M is the molecular weight of the enzyme protein and H is the molecular weight of a proton) had a value of 52501. Since this value is very close to the estimated molecular weight (52503.61) of that portion of the amino acid sequence represented by SEQ ID NO:4 which extends from Leu(205) to Thr(734), it has been revealed that the protein (DHP-A) having asymmetric hydrolase activity for 1,4-DHPDs, which was obtained in Example 4, had been undergone processing at its C-terminus and consisted mainly of a protein terminating at Thr(724) (see SEQ ID NO:7).

EXAMPLE 9

Preparation Process 0.45 ml of a frozen stock culture of *S. viridosporus* A-914(pDE88)-5 strain was inoculated into a 250 ml flask containing 30 ml of C medium, and incubated at 28° C. on a rotary shaker for 45 hours to obtain a seed culture. Then, 60 ml of the seed culture thus obtained was inoculated into 15 liters of a culture medium prepared by removing thiopeptin from C medium and adding 0.09% KM-75 and 0.09% Adecanol LG-126 thereto as anti-foaming agents, and incubated at 28° C. for 5 days. The resulting culture was filtered to obtain 9.5 liters of filtrate. Using a UF membrane, this filtrate was concentrated about fourfold to obtain a DHP-A enzyme solution. Then, 74 g of sodium chloride and 12.8 ml of a DMSO solution containing 60 mg/ml o-phenathroline were added to the 1,280 ml of the above enzyme solution. The resulting mixture was placed in a reaction vessel fitted with a pH-stat, and stirred at 30° C. under an atmosphere of nitrogen while its pH was being adjusted to 8.5–8.6 with 1 N sodium hydroxide. Then, a solution prepared by dissolving 36 g of P-902 in 480 ml of 50 mM Tris-HCl buffer (pH 8.5) was added thereto at a rate of 26.64 ml/hr. over a period of 18 hours. Thirty-four hours after the start of the reaction, an equal amount of ethyl acetate was added to the reaction mixture. The resulting aqueous layer was adjusted to pH 2.0 and extracted twice with an equal amount of ethyl acetate. The combined ethyl acetate layer was washed with distilled water and dried with anhydrous sodium sulfate. After the desiccating agent was filtered off, the filtrate was concentrated to dryness. The resulting yellow solid was evaporated to dryness under reduced pressure to obtain 25.0 g of P-903.

An optical purity test of P-903 thus obtained was carried out. Specifically, a 100 µg/ml solution of P-903 was subjected to HPLC analysis under the following conditions. The column comprised ES-OVM (4.6 I.D.×150 mm), the mobile phase comprised 2-PrOH-0.02 M $KH_2PO_4$ (20:80), the column temperature was 35° C., the flow rate was 1.0 ml/min., the ultraviolet wavelength of the detector was 350 nm, and the amount of test sample injected was 10 µl. Under these conditions, the retention times of (S)-P-903 and (R)-P-903 were 14–15 minutes and 16–17 minutes, respectively.

P-902 and P-903 are represented by the following formulae.

(P-902)

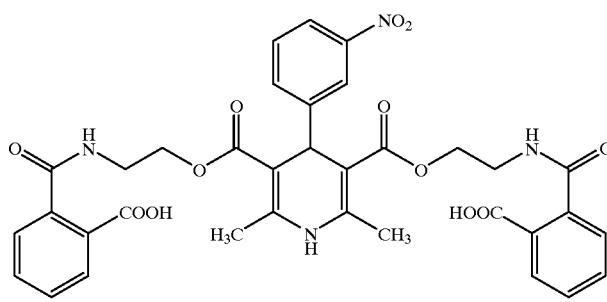

(P-903)

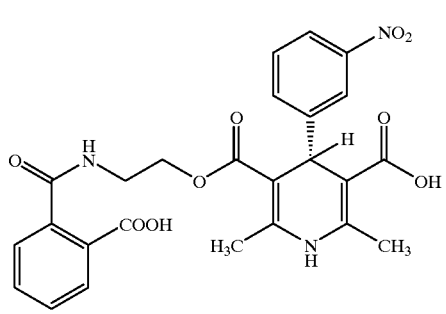

EXAMPLE 10

Figure 7:
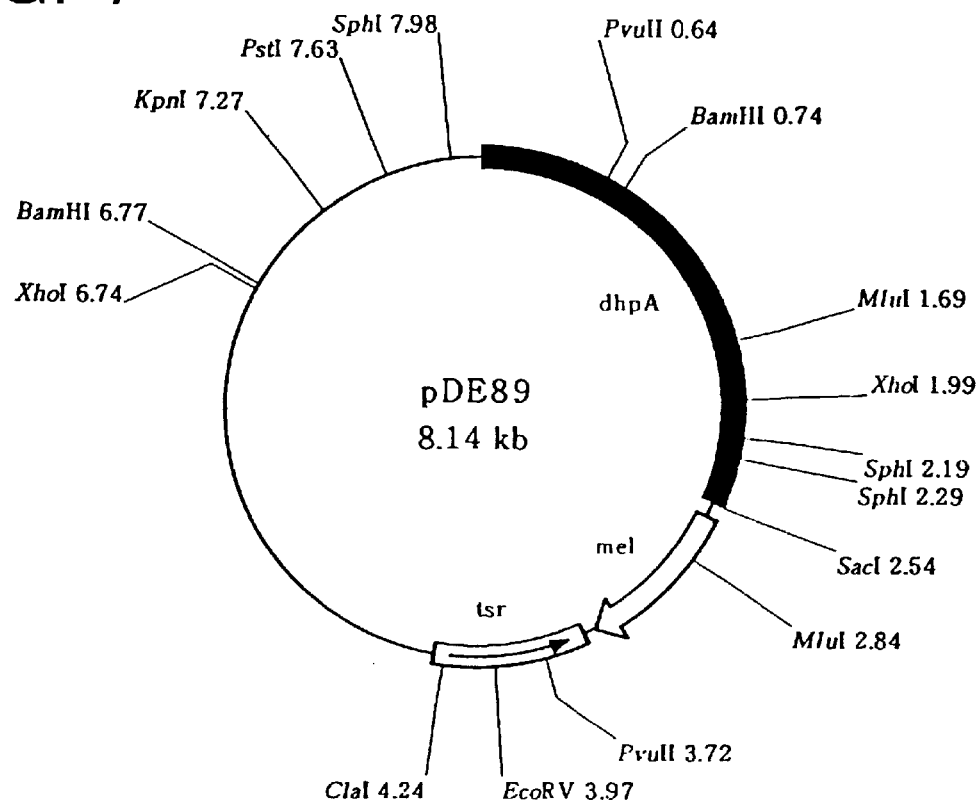
FIG. 7 is a diagram showing the structure of the plasmid pDE89.
Figure 8:
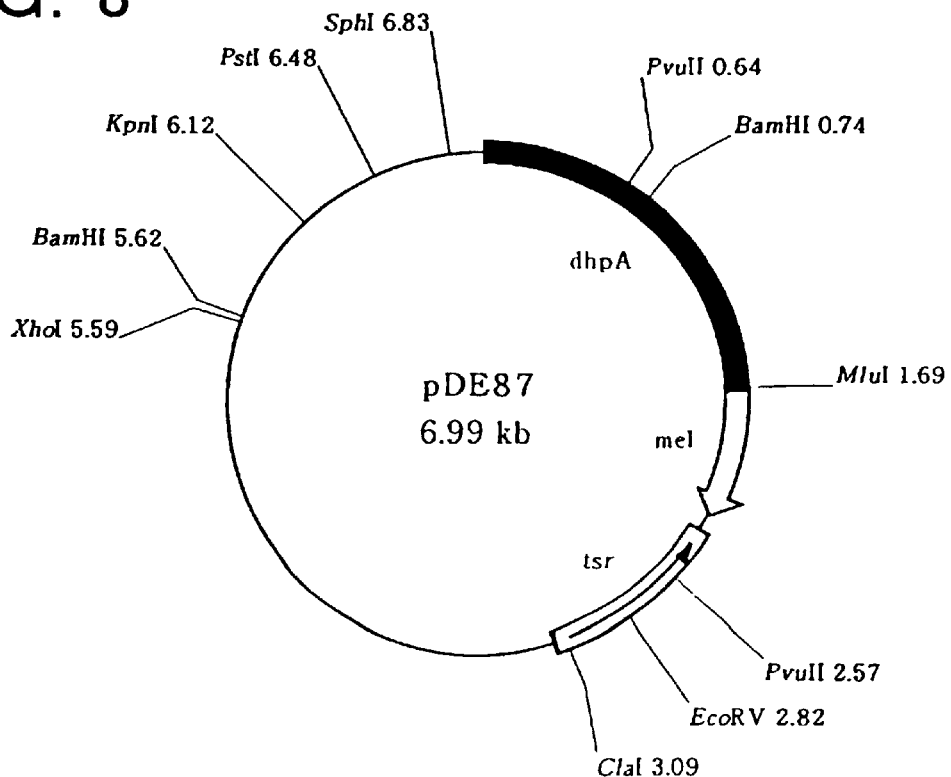
FIG. 8 is a diagram showing the structure of the plasmid pDE87.

Limitation of the dhpA Gene Region Essential for the Expression of a Protein Having Asymmetric Hydrolase Activity for 1,4-DHPDs in the Above-Described Host-Vector System Since *Streptomyces lividans* 66 transformed with pDE88 expressed a protein having asymmetric hydrolase activity for 1,4-DHPDs as described previously, it was believed that the region essential for the expression of the activity was present in the 3.0 kb Sau3AI-inserted fragment contained in pDE88. In order to further limit this region, pDE89 (FIG. 7) and pDE87 (FIG. 8) were constructed. Specifically, 0.2 µg of pDE88 was digested with SacI, and the resulting DNA fragments were subjected to an autocyclization reaction by using a Ligation Kit version 2 (manufactured by Takara Shuzo Co., Ltd.). *Streptomyces lividans* 66 was transformed with this reaction solution, and the plasmid pDE89 was prepared from the resulting transformants according to the method described in the laboratory manual of Hopwood et al. which was already mentioned in Example 1. pDE89 is a plasmid comprising pDE88 from which a 0.64 kb SacI fragment has been deleted.

pDE87 was prepared in the same manner as described above for pDE89, except that pDE88 was digested with MluI in place of SacI. pDE87 is a plasmid comprising pDE88 from which a 1.8 kb MluI fragment has been deleted.

*Streptomyces lividans* 66 transformed with pDE89 exhibited asymmetric hydrolase activity for 1,4-DHPDs, but *Streptomyces lividans* 66 transformed with pDE87 did not exhibit asymmetric hydrolase activity for 1,4-DHPDs. This suggests that the region essential for the expression of a protein having asymmetric hydrolase activity for 1,4-DHPDs is limited to the 2.5 kb region between the SacI and Sau3AI sites and that the MluI site contained therein is required for the expression of the activity.

EXAMPLE 11

Subcloning of the dhpA Gene into a Sequencing Vector (pDE91)

Figure 9:
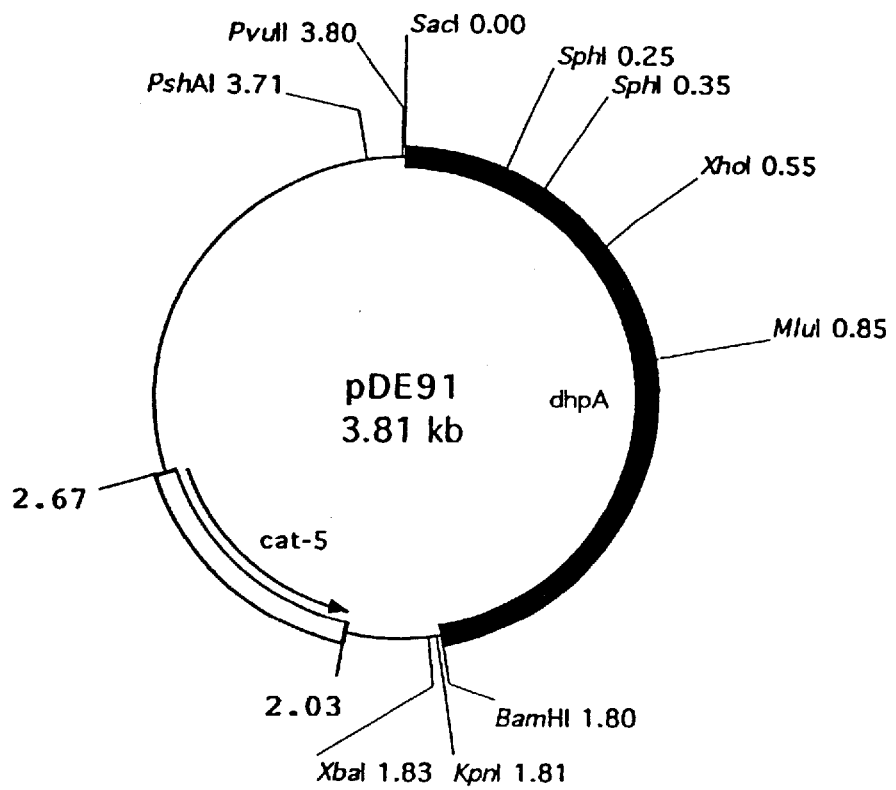
FIG. 9 is a diagram showing the structure of the plasmid pDE91, in which cat-5 represents the chloramphenicol resistance gene.

1 µg of pDE88 was digested with SacI and BamHI. This digestion product was mixed with 0.2 µg of the SacI-BamHI digestion product of the vector plasmid pKF3 (manufactured by Takara Shuzo Co., Ltd.) and ligated thereto by using a Ligation Kit Version 2 (manufactured by Takara Shuzo Co., Ltd.). After completion of the reaction, *Escherichia coli* TH2 competent cells (manufactured by Takara Shuzo Co., Ltd.) were transformed with the resulting solution, and cultured on a recombinant selective medium (1% Bacto Trypton, 0.5% yeast extract, 0.5% NaCl, 50 µg/ml streptomycin sulfate, 12 µg/ml chloramphenicol, pH 7.5). Then, the plasmid pDE91 (FIG. 9) was prepared from a strain grown on the aforesaid medium. pDE91 is a plasmid comprising pKF3 into which a 1.8 kb SacI-BamHI fragment derived from pDE88 has been inserted.

(pDE92)

Figure 10:
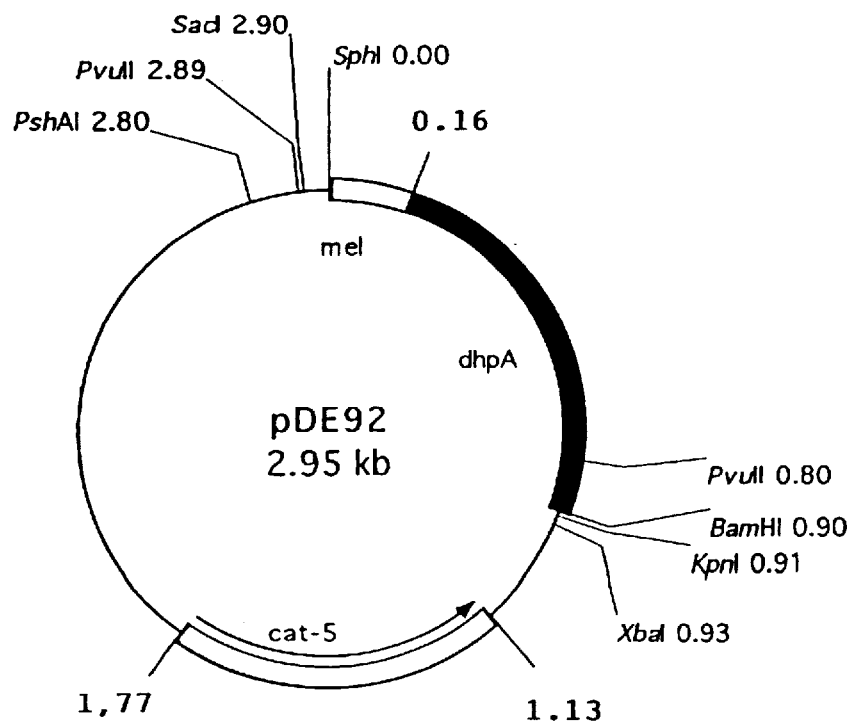
FIG. 10 is a diagram showing the structure of the plasmid pDE92.

1 µg of pDE88 was digested with BamHI and SphI. This digestion product was mixed with 0.2 µg of the BamHI-SphI digestion product of pKF3. Thereafter, ligation and transformation were carried out in the same manner as described in connection with the construction of pDE91. Then, the plasmid pDE92 (FIG. 10) was prepared from the resulting strain. pDE92 is a plasmid comprising pKF3 into which a 0.9 kb BamHI-SphI fragment derived from pDE88 has been inserted.

EXAMPLE 12

Determination of the Base Sequence of the dhpA Gene

1 µg portions of pDE91 were placed in seven tubes and separately digested with PshBI and SacI, PshBI and SphI, PshBI and XHoI, PshBI and MluI, XbaI and MluI, XbaI and XhoI, or XbaI and SphI. Then, using a DNA Blunting Kit (manufactured by Takara Shuzo Co., Ltd.), they were subjected to a DNA end blunting reaction and an autocyclization reaction. E. coli TH2 competent cells were transformed with these solutions, and deletion plasmids were prepared from the strains thus obtained. Moreover, 5 µg of pDE92 was digested with BamHI and KpnI, and then treated with exonuclease III/S1 nuclease to shave off 400 b (base pair) DNA from the BamHI end. Similarly, 5 µg of pDE92 was digested with XhoI and SacI, treated with exonuclease III/S1 nuclease to shave off 160 b and 450 b DNA from the XhoI end, and further digested with PshBI. Then, using a DNA Blunting Kit (manufactured by Takara Shuzo Co., Ltd.), these deletion DNA fragments were subjected to a DNA end blunting reaction and an autocyclization reaction. E. coli TH2 competent cells were transformed with these solutions, and deletion plasmids were prepared from the strains thus obtained. Using these various deletion plasmids, pDE91 and pDE92 as templates, the base sequences thereof were determined with a Model 377 DNA Sequencer (manufactured by Applied Biosystems Inc.). By compiling the sequence data on the various plasmids, the 2539 b base sequence extending from the SacI site to the Sau3AI site and constituting the region essential for the expression of asymmetric hydrolase activity for 4-substituted 1,4-DHPDs as shown in Example 10 was determined.

On the basis of the base sequence so determined, an open reading frame (ORF) was sought according to the method of Bibb et al. [Gene, 30, 157 (1984)]. As a result, an ORF having the sequence represented by SEQ ID NO:1 in the Sequence Listing was found. This sequence included the MluI site (the 858–863 positions in the DNA sequence) shown in Example 8. The dhpA gene begins at the 338 position (GTG) in the DNA sequence of SEQ ID NO:1, but no termination codon was found in a downstream region extending from that position to the end determined in Example 10, i.e., the 2539 position [C (cytosine) in GATC of the Sau3AI site] in the DNA sequence of SEQ ID NO:1.

On the basis of the structure of pDE88, a sequence derived from the vector pIJ702 [i.e., the melanin-producing gene (mel) region derived from *Streptomyces antibioticus*] is connected on the downstream side of the aforesaid end in the direction opposite to that of the dhpA gene. With consideration for the base sequence of the mel gene which was reported by Bernan et al. [Gene, 37, 101 (1985)], a termination codon (TAA) for the ORF continuing from the dhpA gene was found in this mel region at the 2807 position of the DNA sequence represented by SEQ ID NO:2. An amino acid sequence was determined from the DNA sequence corresponding to the translational region extending up to this position, and is shown in SEQ ID NO:1 together with the DNA sequence. The same amino acid sequence is also shown as SEQ ID NO:2. Of the sequences shown in SEQ ID NO:1, a base sequence (the 1–2539 positions in the DNA sequence of SEQ ID NO:1) required for the expression of a protein having the function of the dhpA gene (i.e., asymmetric hydrolase activity for 1,4-DHPDs) in the aforesaid host-vector system and the corresponding amino acid sequence are shown in SEQ ID NO:3. The same amino acid sequence is also shown as SEQ ID NO:4.

According to the present invention, there are provided genes encoding proteins having asymmetric hydrolase activity for 1,4-DHPDs which genes can enhance the efficiency of the production of such proteins with the aid of microorganisms. Moreover, the present invention also provides expression plasmids having such a gene integrated thereinto and transformants obtained by using such an expression plasmid. Furthermore, according to the present invention, proteins having asymmetric hydrolase activity for 1,4-DHPDs can be efficiently prepared by using such transformants. Since the proteins having asymmetric hydrolase activity for 1,4-DHPDs in accordance with the present invention have low protease activity, they are highly stable under various reaction conditions and hence favorable for the synthesis of optically active 1,4-dihydropyridine derivatives on an industrial scale.

Accordingly, the present invention is useful in the field of the preparation of various compounds with the aid of microorganisms and in the field of the pharmaceutical industry.

What is claimed is:

1. An isolated polypeptide having asymmetric hydrolase activity for 4-substituted 1,4-dihydropyridine derivatives (1,4-DBPDs) and comprising amino acid 29 (Asp) to amino acid 238 (Ser) of SEQ ID NO:7.

2. The polypeptide as set forth in claim 1, comprising the amino acid sequence selected from the group consisting of (a) SEQ ID No:7, (b) amino acid 1 (Leu) to amino acid 518 (Ser) of SEQ ID No:7, (c) amino acid 1 (Leu) to amino acid 512 (Pro) of SEQ ID No:7, (d) SEQ ID No:7 and amino acid 725 (Ile) to amino acid 734 (Ile) of SEQ ID No:4 added to the C-terminus of SEQ ID No:7, (e) SEQ ID No:2, and (f) SEQ ID No:4.

3. A polypeptide having asymmetric hydrolase activity for 1,4-DHPDs, which is obtained by (a) transforming a host microorganism with a plasmid comprising a polynucleotide which encodes at least amino acid 29 (Asp) to amino acid 238 (Ser) of SEQ ID No:7, (b) culturing the transformed host microorganism in a nutrient medium, and (c) recovering the polypeptide having asymmetric hydrolase activity for 1,4-DHPDs from the resulting culture.

4. A method for preparing optically active (4R)-1,4-dihydro-2,6-dimethyl-4-(nitrophenyl)-pyridine-3,5-dicarboxylic acid monoester derivatives which comprises:

contacting the polypeptide of claim 1 with a compound of the formula

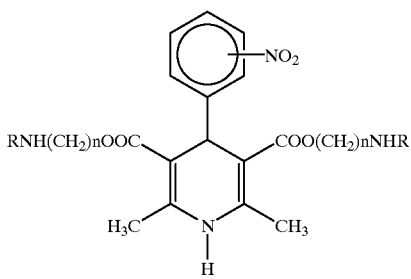

(I)

wherein R is a lower alkanoyl group, a heterocyclic carbonyl group, a halogen-substituted acetyl group, an alkoxyacetyl group, an aryloxyacetyl group, a substituted or unsubstituted phenyl-lower alkanoyl group, a phenyl-substituted or unsubstituted lower alkenoyl group, an alkoxy- or alkenyloxycarbonyl group, an aralkyloxycarbonyl group or organic sulfonyl group, and n is an integer of 2 to 4, or a salt thereof in an aqueous medium, and recovering the optically active 4-substituted 1,4-dihydropyridine compound of the formula

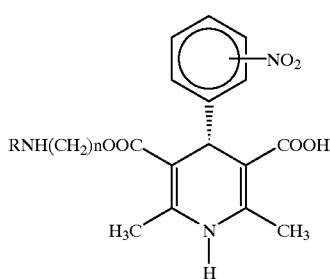

(II)

wherein R and n have the same meanings as described above, or a salt thereof.

5. The method as claimed in claim 4, wherein the polypeptide has the amino acid sequence of SEQ ID NO:7.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 2809 base pairs
      (B) TYPE: nucleic acid
      (C) STRANDEDNESS: double
      (D) TOPOLOGY: linear (ii) MOLECULE TYPE: genomic DNA (vi) ORIGINAL SOURCE:
      (A) ORGANISM: Streptomyces viridosporus
      (B) STRAIN: A-914

(vi) ORIGINAL SOURCE:
      (A) ORGANISM: Streptomyces antibioticus
      (B) STRAIN:

(ix) FEATURE:

(A) NAME/KEY: CDS
        (B) LOCATION: 338...2539
        (C) IDENTIFICATION METHOD: E (ix) FEATURE:
        (A) NAME/KEY: CDS
        (B) LOCATION: 2540...2809
        (C) IDENTIFICATION METHOD: P (xi) SEQUENCE DESCRIPTION: SEQ ID NO:1:

```
GAGCTCGGGC TCACCTTCGT CATGGTCACC CACGACTCGG CGATCGCGCG GAAGGCCCCG        60

CGCCTGGCGA CGATCCGCGA GGGACGGATC ACCGTGCGGG AGAACACCGG GGCCTGAGCC       120

GGCGAGGTCC CACCACGCGG TTCTGTAACG GAGTTCCGGC GGTGACGTTA CAGTCGCCCG       180

GCGACTTGCC CACCTTTTCC ACAGCCCTTG AGGCGCTTGA TCACCCCTCG GCATACTGCG       240

TGCTCCGGGG GGTGCGCGCA TGCGTACGAG ACCACCCCCG ACCGGGTGAC GGGGAGTTCA       300

CCCGGCAACT CCGCTAGGGG GAACCTTGCG CAGACAA GTG AAA AGA GCA TGC GCG        355
                                         Met Lys Arg Ala Cys Ala
                                          1               5

GCC ACG GTC GCC ACG GCC GCC GCC GTG GCC CTC GCG GCC GGC ATG ACC         403
Ala Thr Val Ala Thr Ala Ala Ala Val Ala Leu Ala Ala Gly Met Thr
             10                  15                  20

GGA CCG GCG GCG GCG AGC GGG GAG CAC ACG GCC GCC GCC GGA CAG CCG         451
Gly Pro Ala Ala Ala Ser Gly Glu His Thr Ala Ala Ala Gly Gln Pro
         25                  30                  35

TCG GCG AAG GCG TCG GCG AAG ACG TCC TCG CTC AAG GCC ACG CAG CAC         499
Ser Ala Lys Ala Ser Ala Lys Thr Ser Ser Leu Lys Ala Thr Gln His
     40                  45                  50

ATC ACA CTG ATC ACC GGC GAC CGG GTC GCC GTG GAC GCC ACG GGC CGC         547
Ile Thr Leu Ile Thr Gly Asp Arg Val Ala Val Asp Ala Thr Gly Arg
 55                  60                  65                  70

GTC GTC GGC CTC GAG AGG GCC GAG GGG CGG GAA CAC ATA CCC GTC CAG         595
Val Val Gly Leu Glu Arg Ala Glu Gly Arg Glu His Ile Pro Val Gln
                 75                  80                  85

ATC CGC AAG GTC GAC GGC CAC ACC CTC GTG CTG CCG GCG GAC GCC GCC         643
Ile Arg Lys Val Asp Gly His Thr Leu Val Leu Pro Ala Asp Ala Ala
             90                  95                 100

CGG CTG GTC GCG AGC GGC AAG CTC GAC CGG CGG CTC TTC GAC ATC ACC         691
Arg Leu Val Ala Ser Gly Lys Leu Asp Arg Arg Leu Phe Asp Ile Thr
        105                 110                 115

GAA CTC GGC AAG GCC GCG ACC CGC AAC TCC CAG AAA CAG GGA CTG AAG         739
Glu Leu Gly Lys Ala Ala Thr Arg Asn Ser Gln Lys Gln Gly Leu Lys
    120                 125                 130

GTC ATC GTC GGC TAC CAG GGC GCC GCA CGG GCC GCC AAG GCC GAG GTC         787
Val Ile Val Gly Tyr Gln Gly Ala Ala Arg Ala Ala Lys Ala Glu Val
135                 140                 145                 150

CGC GAA GCG GGC GAA CTC CGC CGG ACC CTG ACG TCC CTG AAC GCG GAC         835
Arg Glu Ala Gly Glu Leu Arg Arg Thr Leu Thr Ser Leu Asn Ala Asp
                155                 160                 165

GCG GTG CGG ACC CCG CAC GAG GAC GCG TCC GAG CTG TGG GAC GCC GTC         883
Ala Val Arg Thr Pro His Glu Asp Ala Ser Glu Leu Trp Asp Ala Val
            170                 175                 180

ACC AAC GGC GAC CGG ACC GCC TCC GGC ATC GCC CAC GTC TGG CTG GAC         931
Thr Asn Gly Asp Arg Thr Ala Ser Gly Ile Ala His Val Trp Leu Asp
        185                 190                 195

GGG GTC CGC AGG GCC GCC CTC GAC ACG TCC GTC GGG CAG ATC GGC GCC         979
Gly Val Arg Arg Ala Ala Leu Asp Thr Ser Val Gly Gln Ile Gly Ala
    200                 205                 210

CCC AAG GCG TGG TCC GCC GGC TAC GAC GGC AAG GGC GTG AAG ATC GCC        1027
Pro Lys Ala Trp Ser Ala Gly Tyr Asp Gly Lys Gly Val Lys Ile Ala
```

-continued

```
             215                 220                 225                 230
GTC CTG GAC ACC GGT GTC GAC ACG AGC CAT CCG GAC CTG AAG GGC CGG         1075
Val Leu Asp Thr Gly Val Asp Thr Ser His Pro Asp Leu Lys Gly Arg
                    235                 240                 245

GTG ACC GCG TCC AAG AAC TTC ACC GCC GCG CCC GGC GCC GGC GAC AAG         1123
Val Thr Ala Ser Lys Asn Phe Thr Ala Ala Pro Gly Ala Gly Asp Lys
                250                 255                 260

GTG GGC CAC GGC ACC CAC GTC GCC TCG ATC GCG GCG GGC ACG GGC GCC         1171
Val Gly His Gly Thr His Val Ala Ser Ile Ala Ala Gly Thr Gly Ala
            265                 270                 275

CAG TCC AAG GGC AAG TAC AAG GGC GTC GCA CCC GGC GCC GCG ATC CTC         1219
Gln Ser Lys Gly Lys Tyr Lys Gly Val Ala Pro Gly Ala Ala Ile Leu
        280                 285                 290

AAC GGC AAG GTC CTC GAC GAC TCC GGT TTC GGC GAC GAC TCC GGC ATC         1267
Asn Gly Lys Val Leu Asp Asp Ser Gly Phe Gly Asp Asp Ser Gly Ile
295                 300                 305                 310

CTC GCC GGC ATG GAG TGG GCG GCC GCG CAG GGC GCC GAC GTC GTC AAC         1315
Leu Ala Gly Met Glu Trp Ala Ala Ala Gln Gly Ala Asp Val Val Asn
                315                 320                 325

ATG AGC CTG GGC GGC ATG GAC ACA CCG GAG ACC GAC CCG CTG GAG GCG         1363
Met Ser Leu Gly Gly Met Asp Thr Pro Glu Thr Asp Pro Leu Glu Ala
            330                 335                 340

GCG GTC GAC AAG CTG TCC GCC GAG AAG GGC GTC CTG TTC GCC ATC GCG         1411
Ala Val Asp Lys Leu Ser Ala Glu Lys Gly Val Leu Phe Ala Ile Ala
        345                 350                 355

GCC GGC AAC GAG GGC CCG GAG TCG ATC GGT TCG CCC GGC AGC GCG GAC         1459
Ala Gly Asn Glu Gly Pro Glu Ser Ile Gly Ser Pro Gly Ser Ala Asp
        360                 365                 370

GCC GCC CTC ACC GTC GGC GCC GTC GAC GAC AAG GAC AAG CTC GCC GAC         1507
Ala Ala Leu Thr Val Gly Ala Val Asp Asp Lys Asp Lys Leu Ala Asp
375                 380                 385                 390

TTC TCC TCC ACC GGC CCC CGC CTC GGC GAC GGC GCC ATC AAG CCG GAC         1555
Phe Ser Ser Thr Gly Pro Arg Leu Gly Asp Gly Ala Ile Lys Pro Asp
                395                 400                 405

GTC ACC GCT CCC GGC GTG GAC ATC ACG GCC GCC TCG GCG GAG GGC AAC         1603
Val Thr Ala Pro Gly Val Asp Ile Thr Ala Ala Ser Ala Glu Gly Asn
            410                 415                 420

GAC ATC GGC CAG GAG GTC GGT GAG GGA CCG GCC GGC TAC ATG ACC ATC         1651
Asp Ile Gly Gln Glu Val Gly Glu Gly Pro Ala Gly Tyr Met Thr Ile
        425                 430                 435

TCC GGC ACG TCG ATG GCG ACC CCG CAC GTC GCG GGC GCG GCG GCC CTC         1699
Ser Gly Thr Ser Met Ala Thr Pro His Val Ala Gly Ala Ala Ala Leu
        440                 445                 450

CTG AAG CAG CAG CAC CCC GAC TGG ACC TCC GCC GAA CTG AAG GGC GCG         1747
Leu Lys Gln Gln His Pro Asp Trp Thr Ser Ala Glu Leu Lys Gly Ala
455                 460                 465                 470

CTC ACC GGC TCC ACC AAG GGC GGC AAG TAC ACC CCG TTC GAG CAG GGT         1795
Leu Thr Gly Ser Thr Lys Gly Gly Lys Tyr Thr Pro Phe Glu Gln Gly
                475                 480                 485

TCG GGC CGG ATC CAG GCC GAC AAG GCG CTC CAG CAG ACC GTG ATC GCC         1843
Ser Gly Arg Ile Gln Ala Asp Lys Ala Leu Gln Gln Thr Val Ile Ala
            490                 495                 500

GAC CCG GTC TCG GTG AGC TTC GGC GTC CAG CAG TGG CCG CAC ACC GAC         1891
Asp Pro Val Ser Val Ser Phe Gly Val Gln Gln Trp Pro His Thr Asp
        505                 510                 515

GAC GAG CCG GTC ACC AAG CAG CTG ACC TAC CGC AAC CTC GGC ACC CAG         1939
Asp Glu Pro Val Thr Lys Gln Leu Thr Tyr Arg Asn Leu Gly Thr Gln
        520                 525                 530

GAC GTC ACG CTG AAG CTG ACG TCG ACC GCC ACC GAC CCC AAG GGC AAG         1987
```

```
                Asp Val Thr Leu Lys Leu Thr Ser Thr Ala Thr Asp Pro Lys Gly Lys
                535                 540                 545                 550

GCG GCC CCG GCG GGC TTC TTC ACG CTG GGC GCC ACC ACG GTG ACC GTC      2035
                Ala Ala Pro Ala Gly Phe Phe Thr Leu Gly Ala Thr Thr Val Thr Val
                                555                 560                 565

CCG GCG GGC GGC AGC GCC TCC GTC GAC ATG ACC GCC GAC ACC CGG CTC      2083
                Pro Ala Gly Gly Ser Ala Ser Val Asp Met Thr Ala Asp Thr Arg Leu
                            570                 575                 580

GGC GGC ACG GTG GAC GGC GCG TAC TCG GCG TAC GTG GTC GCC ACG GGC      2131
                Gly Gly Thr Val Asp Gly Ala Tyr Ser Ala Tyr Val Val Ala Thr Gly
                        585                 590                 595

GGC GGG CAG ACG GTC CGC ACG GCC GCC GCG GTG CAG CGC GAG GTC GAG      2179
                Gly Gly Gln Thr Val Arg Thr Ala Ala Ala Val Gln Arg Glu Val Glu
                    600                 605                 610

TCG TAC GAC GTG ACC GTC CGG CAC ATC GGC CGG GAC GGC AAG CCC ACG      2227
                Ser Tyr Asp Val Thr Val Arg His Ile Gly Arg Asp Gly Lys Pro Thr
                615                 620                 625                 630

ACC GAA CAC CTC ACC GAC CTG ATC GGC TAC GCG GGC CTG GGC TCC GGC      2275
                Thr Glu His Leu Thr Asp Leu Ile Gly Tyr Ala Gly Leu Gly Ser Gly
                                635                 640                 645

CGC GGT TAC GGC GCC CCG GCC ACC GAC ACC GCC ACC CTG CGC CTG CCC      2323
                Arg Gly Tyr Gly Ala Pro Ala Thr Asp Thr Ala Thr Leu Arg Leu Pro
                            650                 655                 660

AAG GGC ACC TAC CTG GTG GAC TCC TGG ATC GCC AAG GAC TTC GGG ACG      2371
                Lys Gly Thr Tyr Leu Val Asp Ser Trp Ile Ala Lys Asp Phe Gly Thr
                        665                 670                 675

CTC AAG GGC GGC ATC GAC TGG CTG GTC CAG CCG AAG CTG AGC GTC ACC      2419
                Leu Lys Gly Gly Ile Asp Trp Leu Val Gln Pro Lys Leu Ser Val Thr
                    680                 685                 690

AAG GAC ACC ACG CTG ACA CTC GAC GCA CGC ACC ACC AAG GCG GCG GAC      2467
                Lys Asp Thr Thr Leu Thr Leu Asp Ala Arg Thr Thr Lys Ala Ala Asp
                695                 700                 705                 710

ATC ACC GTG CCG GAC CCC AAG GCC AAG CCG CTC TCC GCG ACC ATC GGC      2515
                Ile Thr Val Pro Asp Pro Lys Ala Lys Pro Leu Ser Ala Thr Ile Gly
                                715                 720                 725

TAC ACC TAC GAC ACG GCG GGG ATC TCG TCG AAG GCG GCG GGG GCG CCG      2563
                Tyr Thr Tyr Asp Thr Ala Gly Ile Ser Ser Lys Ala Ala Gly Ala Pro
                            730                 735                 740

GAC GCG GCC GGG TTC CCG GGG ACC TCG GGG GTG TGG TGC CCC CGA TCG      2611
                Asp Ala Ala Gly Phe Pro Gly Thr Ser Gly Val Trp Cys Pro Arg Ser
                        745                 750                 755

TCC GCG CGG GCG GCG GGA AGG GCG ACC AGC GGG ACA CCG GCG GCG ACG      2659
                Ser Ala Arg Ala Ala Gly Arg Ala Thr Ser Gly Thr Pro Ala Ala Thr
                    760                 765                 770

ACG GCT GCG GCG CCG AGC GCG CGA CGA CGG GTG AGT TCC GGC ATG CGG      2707
                Thr Ala Ala Ala Pro Ser Ala Arg Arg Arg Val Ser Ser Gly Met Arg
                775                 780                 785                 790

GAC CTC CTG GGG TGC GTT GGG TTG ACG ACC CCG CAT ACC TAT CGA CCG      2755
                Asp Leu Leu Gly Cys Val Gly Leu Thr Thr Pro His Thr Tyr Arg Pro
                                795                 800                 805

GAG GAG AAG GGG AGA AAT CGG CCC GGA CCG GTT GGC CGC GAT CCG GAC      2803
                Glu Glu Lys Gly Arg Asn Arg Pro Gly Pro Val Gly Arg Asp Pro Asp
                            810                 815                 820

AAT TAA                                                              2809
                Asn
                823

(2) INFORMATION FOR SEQ ID NO:2:

(i) SEQUENCE CHARACTERISTICS:
```

(A) LENGTH: 823 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

```
Met Lys Arg Ala Cys Ala Ala Thr Val Ala Thr Ala Ala Val Ala
 1               5                  10                  15

Leu Ala Ala Gly Met Thr Gly Pro Ala Ala Ser Gly Glu His Thr
                 20                  25                  30

Ala Ala Ala Gly Gln Pro Ser Ala Lys Ala Ser Ala Lys Thr Ser Ser
                 35                  40                  45

Leu Lys Ala Thr Gln His Ile Thr Leu Ile Thr Gly Asp Arg Val Ala
 50                              55                  60

Val Asp Ala Thr Gly Arg Val Val Gly Leu Glu Arg Ala Glu Gly Arg
 65                  70                  75                  80

Glu His Ile Pro Val Gln Ile Arg Lys Val Asp Gly His Thr Leu Val
                 85                  90                  95

Leu Pro Ala Asp Ala Ala Arg Leu Val Ala Ser Gly Lys Leu Asp Arg
                100                 105                 110

Arg Leu Phe Asp Ile Thr Glu Leu Gly Lys Ala Ala Thr Arg Asn Ser
                115                 120                 125

Gln Lys Gln Gly Leu Lys Val Ile Val Gly Tyr Gln Gly Ala Ala Arg
130                             135                 140

Ala Ala Lys Ala Glu Val Arg Glu Ala Gly Glu Leu Arg Arg Thr Leu
145                 150                 155                 160

Thr Ser Leu Asn Ala Asp Ala Val Arg Thr Pro His Glu Asp Ala Ser
                165                 170                 175

Glu Leu Trp Asp Ala Val Thr Asn Gly Asp Arg Thr Ala Ser Gly Ile
                180                 185                 190

Ala His Val Trp Leu Asp Gly Val Arg Arg Ala Ala Leu Asp Thr Ser
                195                 200                 205

Val Gly Gln Ile Gly Ala Pro Lys Ala Trp Ser Ala Gly Tyr Asp Gly
                210                 215                 220

Lys Gly Val Lys Ile Ala Val Leu Asp Thr Gly Val Asp Thr Ser His
225                 230                 235                 240

Pro Asp Leu Lys Gly Arg Val Thr Ala Ser Lys Asn Phe Thr Ala Ala
                245                 250                 255

Pro Gly Ala Gly Asp Lys Val Gly His Gly Thr His Val Ala Ser Ile
                260                 265                 270

Ala Ala Gly Thr Gly Ala Gln Ser Lys Gly Lys Tyr Lys Gly Val Ala
                275                 280                 285

Pro Gly Ala Ala Ile Leu Asn Gly Lys Val Leu Asp Asp Ser Gly Phe
                290                 295                 300

Gly Asp Asp Ser Gly Ile Leu Ala Gly Met Glu Trp Ala Ala Ala Gln
305                 310                 315                 320

Gly Ala Asp Val Val Asn Met Ser Leu Gly Gly Met Asp Thr Pro Glu
                325                 330                 335

Thr Asp Pro Leu Glu Ala Ala Val Asp Lys Leu Ser Ala Glu Lys Gly
                340                 345                 350

Val Leu Phe Ala Ile Ala Ala Gly Asn Glu Gly Pro Glu Ser Ile Gly
                355                 360                 365

Ser Pro Gly Ser Ala Asp Ala Ala Leu Thr Val Gly Ala Val Asp Asp
```

```
              370            375             380
Lys Asp Lys Leu Ala Asp Phe Ser Ser Thr Gly Pro Arg Leu Gly Asp
385                 390                 395                 400
Gly Ala Ile Lys Pro Asp Val Thr Ala Pro Gly Val Asp Ile Thr Ala
                405                 410                 415
Ala Ser Ala Glu Gly Asn Asp Ile Gly Gln Glu Val Gly Glu Gly Pro
            420                 425                 430
Ala Gly Tyr Met Thr Ile Ser Gly Thr Ser Met Ala Thr Pro His Val
        435                 440                 445
Ala Gly Ala Ala Ala Leu Leu Lys Gln Gln His Pro Asp Trp Thr Ser
    450                 455                 460
Ala Glu Leu Lys Gly Ala Leu Thr Gly Ser Thr Lys Gly Gly Lys Tyr
465                 470                 475                 480
Thr Pro Phe Glu Gln Gly Ser Gly Arg Ile Gln Ala Asp Lys Ala Leu
                485                 490                 495
Gln Gln Thr Val Ile Ala Asp Pro Val Ser Val Ser Phe Gly Val Gln
            500                 505                 510
Gln Trp Pro His Thr Asp Asp Glu Pro Val Thr Lys Gln Leu Thr Tyr
        515                 520                 525
Arg Asn Leu Gly Thr Gln Asp Val Thr Leu Lys Leu Thr Ser Thr Ala
    530                 535                 540
Thr Asp Pro Lys Gly Lys Ala Ala Pro Ala Gly Phe Phe Thr Leu Gly
545                 550                 555                 560
Ala Thr Thr Val Thr Val Pro Ala Gly Gly Ser Ala Ser Val Asp Met
                565                 570                 575
Thr Ala Asp Thr Arg Leu Gly Gly Thr Val Asp Gly Ala Tyr Ser Ala
            580                 585                 590
Tyr Val Val Ala Thr Gly Gly Gly Gln Thr Val Arg Thr Ala Ala Ala
        595                 600                 605
Val Gln Arg Glu Val Glu Ser Tyr Asp Val Thr Val Arg His Ile Gly
    610                 615                 620
Arg Asp Gly Lys Pro Thr Thr Glu His Leu Thr Asp Leu Ile Gly Tyr
625                 630                 635                 640
Ala Gly Leu Gly Ser Gly Arg Gly Tyr Gly Ala Pro Ala Thr Asp Thr
                645                 650                 655
Ala Thr Leu Arg Leu Pro Lys Gly Thr Tyr Leu Val Asp Ser Trp Ile
            660                 665                 670
Ala Lys Asp Phe Gly Thr Leu Lys Gly Gly Ile Asp Trp Leu Val Gln
        675                 680                 685
Pro Lys Leu Ser Val Thr Lys Asp Thr Thr Leu Thr Leu Asp Ala Arg
    690                 695                 700
Thr Thr Lys Ala Ala Asp Ile Thr Val Pro Asp Pro Lys Ala Lys Pro
705                 710                 715                 720
Leu Ser Ala Thr Ile Gly Tyr Thr Tyr Asp Thr Ala Gly Ile Ser Ser
                725                 730                 735
Lys Ala Ala Gly Ala Pro Asp Ala Gly Phe Pro Gly Thr Ser Gly
            740                 745                 750
Val Trp Cys Pro Arg Ser Ser Ala Arg Ala Ala Gly Arg Ala Thr Ser
        755                 760                 765
Gly Thr Pro Ala Ala Thr Thr Ala Ala Pro Ser Ala Arg Arg Arg
    770                 775                 780
Val Ser Ser Gly Met Arg Asp Leu Leu Gly Cys Val Gly Leu Thr Thr
785                 790                 795                 800
```

```
Pro His Thr Tyr Arg Pro Glu Glu Lys Gly Arg Asn Arg Pro Gly Pro
            805                 810                 815
Val Gly Arg Asp Pro Asp Asn
            820         823

(2) INFORMATION FOR SEQ ID NO:3:

(i) SEQUENCE CHARACTERISTICS:
        (A) LENGTH:  2539 base pairs
        (B) TYPE:  nucleic acid
        (C) STRANDEDNESS:  double
        (D) TOPOLOGY:  linear (ii) MOLECULE TYPE: genomic DNA (vi) ORIGINAL SOURCE:
        (A) ORGANISM:  Streptomyces viridosporus
        (B) STRAIN:  A-914

(ix) FEATURE:
        (A) NAME/KEY: CDS
        (B) LOCATION: 338...2539
        (C) IDENTIFICATION METHOD: E (xi) SEQUENCE DESCRIPTION: SEQ ID NO:3:
```

| | |
|---|---:|
| GAGCTCGGGC TCACCTTCGT CATGGTCACC CACGACTCGG CGATCGCGCG GAAGGCCCCG | 60 |
| CGCCTGGCGA CGATCCGCGA GGGACGGATC ACCGTGCGGG AGAACACCGG GGCCTGAGCC | 120 |
| GGCGAGGTCC CACCACGCGG TTCTGTAACG GAGTTCCGGC GGTGACGTTA CAGTCGCCCG | 180 |
| GCGACTTGCC CACCTTTTCC ACAGCCCTTG AGGCGCTTGA TCACCCCTCG GCATACTGCG | 240 |
| TGCTCCGGGG GGTGCGCGCA TGCGTACGAG ACCACCCCCG ACCGGGTGAC GGGGAGTTCA | 300 |

```
CCCGGCAACT CCGCTAGGGG GAACCTTGCG CAGACAA GTG AAA AGA GCA TGC GCG      355
                                         Met Lys Arg Ala Cys Ala
                                           1               5

GCC ACG GTC GCC ACG GCC GCC GCC GTG GCC CTC GCG GCC GGC ATG ACC       403
Ala Thr Val Ala Thr Ala Ala Ala Val Ala Leu Ala Ala Gly Met Thr
            10                  15                  20

GGA CCG GCG GCG GCG AGC GGG GAG CAC ACG GCC GCC GCC GGA CAG CCG       451
Gly Pro Ala Ala Ala Ser Gly Glu His Thr Ala Ala Ala Gly Gln Pro
        25                  30                  35

TCG GCG AAG GCG TCG GCG AAG ACG TCC TCG CTC AAG GCC ACG CAG CAC       499
Ser Ala Lys Ala Ser Ala Lys Thr Ser Ser Leu Lys Ala Thr Gln His
    40                  45                  50

ATC ACA CTG ATC ACC GGC GAC CGG GTC GCC GTG GAC GCC ACG GGC CGC       547
Ile Thr Leu Ile Thr Gly Asp Arg Val Ala Val Asp Ala Thr Gly Arg
55                  60                  65                  70

GTC GTC GGC CTC GAG AGG GCC GAG GGG CGG GAA CAC ATA CCC GTC CAG       595
Val Val Gly Leu Glu Arg Ala Glu Gly Arg Glu His Ile Pro Val Gln
                75                  80                  85

ATC CGC AAG GTC GAC GGC CAC ACC CTC GTG CTG CCG GCG GAC GCC GCC       643
Ile Arg Lys Val Asp Gly His Thr Leu Val Leu Pro Ala Asp Ala Ala
                90                  95                  100

CGG CTG GTC GCG AGC GGC AAG CTC GAC CGG CGG CTC TTC GAC ATC ACC       691
Arg Leu Val Ala Ser Gly Lys Leu Asp Arg Arg Leu Phe Asp Ile Thr
            105                 110                 115

GAA CTC GGC AAG GCC GCG ACC CGC AAC TCC CAG AAA CAG GGA CTG AAG       739
Glu Leu Gly Lys Ala Ala Thr Arg Asn Ser Gln Lys Gln Gly Leu Lys
        120                 125                 130

GTC ATC GTC GGC TAC CAG GGC GCC GCA CGG GCC GCC AAG GCC GAG GTC       787
Val Ile Val Gly Tyr Gln Gly Ala Ala Arg Ala Ala Lys Ala Glu Val
135                 140                 145                 150
```

```
CGC GAA GCG GGC GAA CTC CGC CGG ACC CTG ACG TCC CTG AAC GCG GAC      835
Arg Glu Ala Gly Glu Leu Arg Arg Thr Leu Thr Ser Leu Asn Ala Asp
                155                 160                 165

GCG GTG CGG ACC CCG CAC GAG GAC GCG TCC GAG CTG TGG GAC GCC GTC      883
Ala Val Arg Thr Pro His Glu Asp Ala Ser Glu Leu Trp Asp Ala Val
                170                 175                 180

ACC AAC GGC GAC CGG ACC GCC TCC GGC ATC GCC CAC GTC TGG CTG GAC      931
Thr Asn Gly Asp Arg Thr Ala Ser Gly Ile Ala His Val Trp Leu Asp
                185                 190                 195

GGG GTC CGC AGG GCC GCC CTC GAC ACG TCC GTC GGG CAG ATC GGC GCC      979
Gly Val Arg Arg Ala Ala Leu Asp Thr Ser Val Gly Gln Ile Gly Ala
    200                 205                 210

CCC AAG GCG TGG TCC GCC GGC TAC GAC GGC AAG GGC GTG AAG ATC GCC     1027
Pro Lys Ala Trp Ser Ala Gly Tyr Asp Gly Lys Gly Val Lys Ile Ala
215                 220                 225                 230

GTC CTG GAC ACC GGT GTC GAC ACG AGC CAT CCG GAC CTG AAG GGC CGG     1075
Val Leu Asp Thr Gly Val Asp Thr Ser His Pro Asp Leu Lys Gly Arg
                235                 240                 245

GTG ACC GCG TCC AAG AAC TTC ACC GCC GCG CCC GGC GCC GGC GAC AAG     1123
Val Thr Ala Ser Lys Asn Phe Thr Ala Ala Pro Gly Ala Gly Asp Lys
                250                 255                 260

GTG GGC CAC GGC ACC CAC GTC GCC TCG ATC GCG GCG GGC ACG GGC GCC     1171
Val Gly His Gly Thr His Val Ala Ser Ile Ala Ala Gly Thr Gly Ala
                265                 270                 275

CAG TCC AAG GGC AAG TAC AAG GGC GTC GCA CCC GGC GCC GCG ATC CTC     1219
Gln Ser Lys Gly Lys Tyr Lys Gly Val Ala Pro Gly Ala Ala Ile Leu
    280                 285                 290

AAC GGC AAG GTC CTC GAC GAC TCC GGT TTC GGC GAC GAC TCC GGC ATC     1267
Asn Gly Lys Val Leu Asp Asp Ser Gly Phe Gly Asp Asp Ser Gly Ile
295                 300                 305                 310

CTC GCC GGC ATG GAG TGG GCG GCC GCG CAG GGC GCC GAC GTC GTC ACC     1315
Leu Ala Gly Met Glu Trp Ala Ala Ala Gln Gly Ala Asp Val Val Asn
                315                 320                 325

ATG AGC CTG GGC GGC ATG GAC ACA CCG GAG ACC GAC CCG CTG GAG GCG     1363
Met Ser Leu Gly Gly Met Asp Thr Pro Glu Thr Asp Pro Leu Glu Ala
                330                 335                 340

GCG GTC GAC AAG CTG TCC GCC GAG AAG GGC GTC CTG TTC GCC ATC GCG     1411
Ala Val Asp Lys Leu Ser Ala Glu Lys Gly Val Leu Phe Ala Ile Ala
                345                 350                 355

GCC GGC AAC GAG GGC CCG GAG TCG ATC GGT TCG CCC GGC AGC GCG GAC     1459
Ala Gly Asn Glu Gly Pro Glu Ser Ile Gly Ser Pro Gly Ser Ala Asp
    360                 365                 370

GCC GCC CTC ACC GTC GGC GCC GTC GAC GAC AAG GAC AAG CTC GCC GAC     1507
Ala Ala Leu Thr Val Gly Ala Val Asp Asp Lys Asp Lys Leu Ala Asp
375                 380                 385                 390

TTC TCC TCC ACC GGC CCC CGC CTC GGC GAC GGC GCC ATC AAG CCG GAC     1555
Phe Ser Ser Thr Gly Pro Arg Leu Gly Asp Gly Ala Ile Lys Pro Asp
                395                 400                 405

GTC ACC GCT CCC GGC GTG GAC ATC ACG GCC GCC TCG GCG GAG GGC AAC     1603
Val Thr Ala Pro Gly Val Asp Ile Thr Ala Ala Ser Ala Glu Gly Asn
                410                 415                 420

GAC ATC GGC CAG GAG GTC GGT GAG GGA CCG GCC GGC TAC ATG ACC ATC     1651
Asp Ile Gly Gln Glu Val Gly Glu Gly Pro Ala Gly Tyr Met Thr Ile
    425                 430                 435

TCC GGC ACG TCG ATG GCG ACC CCG CAC GTC GCG GGC GCG GCG GCC CTC     1699
Ser Gly Thr Ser Met Ala Thr Pro His Val Ala Gly Ala Ala Ala Leu
    440                 445                 450

CTG AAG CAG CAG CAC CCC GAC TGG ACC TCC GCC GAA CTG AAG GGC GCG     1747
Leu Lys Gln Gln His Pro Asp Trp Thr Ser Ala Glu Leu Lys Gly Ala
455                 460                 465                 470
```

```
CTC ACC GGC TCC ACC AAG GGC GGC AAG TAC ACC CCG TTC GAG CAG GGT    1795
Leu Thr Gly Ser Thr Lys Gly Gly Lys Tyr Thr Pro Phe Glu Gln Gly
            475                 480                 485

TCG GGC CGG ATC CAG GCC GAC AAG GCG CTC CAG CAG ACC GTG ATC GCC    1843
Ser Gly Arg Ile Gln Ala Asp Lys Ala Leu Gln Gln Thr Val Ile Ala
            490                 495                 500

GAC CCG GTC TCG GTG AGC TTC GGC GTC CAG CAG TGG CCG CAC ACC GAC    1891
Asp Pro Val Ser Val Ser Phe Gly Val Gln Gln Trp Pro His Thr Asp
            505                 510                 515

GAC GAG CCG GTC ACC AAG CAG CTG ACC TAC CGC AAC CTC GGC ACC CAG    1939
Asp Glu Pro Val Thr Lys Gln Leu Thr Tyr Arg Asn Leu Gly Thr Gln
    520                 525                 530

GAC GTC ACG CTG AAG CTG ACG TCG ACC GCC ACC GAC CCC AAG GGC AAG    1987
Asp Val Thr Leu Lys Leu Thr Ser Thr Ala Thr Asp Pro Lys Gly Lys
535                 540                 545                 550

GCG GCC CCG GCG GGC TTC TTC ACG CTG GGC GCC ACC ACG GTG ACC GTC    2035
Ala Ala Pro Ala Gly Phe Phe Thr Leu Gly Ala Thr Thr Val Thr Val
            555                 560                 565

CCG GCG GGC GGC AGC GCC TCC GTC GAC ATG ACC GCC GAC ACC CGG CTC    2083
Pro Ala Gly Gly Ser Ala Ser Val Asp Met Thr Ala Asp Thr Arg Leu
            570                 575                 580

GGC GGC ACG GTG GAC GGC GCG TAC TCG GCG TAC GTG GTC GCC ACG GGC    2131
Gly Gly Thr Val Asp Gly Ala Tyr Ser Ala Tyr Val Val Ala Thr Gly
            585                 590                 595

GGC GGG CAG ACG GTC CGC ACG GCC GCC GCG GTG CAG CGC GAG GTC GAG    2179
Gly Gly Gln Thr Val Arg Thr Ala Ala Ala Val Gln Arg Glu Val Glu
    600                 605                 610

TCG TAC GAC GTG ACC GTC CGG CAC ATC GGC CGG GAC GGC AAG CCC ACG    2227
Ser Tyr Asp Val Thr Val Arg His Ile Gly Arg Asp Gly Lys Pro Thr
615                 620                 625                 630

ACC GAA CAC CTC ACC GAC CTG ATC GGC TAC GCG GGC CTG GGC TCC GGC    2275
Thr Glu His Leu Thr Asp Leu Ile Gly Tyr Ala Gly Leu Gly Ser Gly
            635                 640                 645

CGC GGT TAC GGC GCC CCG GCC ACC GAC ACC GCC ACC CTG CGC CTG CCC    2323
Arg Gly Tyr Gly Ala Pro Ala Thr Asp Thr Ala Thr Leu Arg Leu Pro
            650                 655                 660

AAG GGC ACC TAC CTG GTG GAC TCC TGG ATC GCC AAG GAC TTC GGG ACG    2371
Lys Gly Thr Tyr Leu Val Asp Ser Trp Ile Ala Lys Asp Phe Gly Thr
            665                 670                 675

CTC AAG GGC GGC ATC GAC TGG CTG GTC CAG CCG AAG CTG AGC GTC ACC    2419
Leu Lys Gly Gly Ile Asp Trp Leu Val Gln Pro Lys Leu Ser Val Thr
            680                 685                 690

AAG GAC ACC ACG CTG ACA CTC GAC GCA CGC ACC ACC AAG GCG GCG GAC    2467
Lys Asp Thr Thr Leu Thr Leu Asp Ala Arg Thr Thr Lys Ala Ala Asp
695                 700                 705                 710

ATC ACC GTG CCG GAC CCC AAG GCC AAG CCG CTC TCC GCG ACC ATC GGC    2515
Ile Thr Val Pro Asp Pro Lys Ala Lys Pro Leu Ser Ala Thr Ile Gly
            715                 720                 725

TAC ACC TAC GAC ACG GCG GGG ATC                                    2539
Tyr Thr Tyr Asp Thr Ala Gly Ile
            730         734
```

(2) INFORMATION FOR SEQ ID NO:4:

(i) SEQUENCE CHARACTERISTICS:
        (A) LENGTH: 734 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Lys Arg Ala Cys Ala Ala Thr Val Ala Thr Ala Ala Val Ala
 1               5                  10                  15

Leu Ala Ala Gly Met Thr Gly Pro Ala Ala Ser Gly Glu His Thr
                20                  25                  30

Ala Ala Ala Gly Gln Pro Ser Ala Lys Ala Ser Ala Lys Thr Ser Ser
            35                  40                  45

Leu Lys Ala Thr Gln His Ile Thr Leu Ile Thr Gly Asp Arg Val Ala
     50                  55                  60

Val Asp Ala Thr Gly Arg Val Val Gly Leu Glu Arg Ala Glu Gly Arg
 65                  70                  75                  80

Glu His Ile Pro Val Gln Ile Arg Lys Val Asp Gly His Thr Leu Val
                85                  90                  95

Leu Pro Ala Asp Ala Ala Arg Leu Val Ala Ser Gly Lys Leu Asp Arg
                100                 105                 110

Arg Leu Phe Asp Ile Thr Glu Leu Gly Lys Ala Ala Thr Arg Asn Ser
            115                 120                 125

Gln Lys Gln Gly Leu Lys Val Ile Val Gly Tyr Gln Gly Ala Ala Arg
    130                 135                 140

Ala Ala Lys Ala Glu Val Arg Glu Ala Gly Glu Leu Arg Arg Thr Leu
145                 150                 155                 160

Thr Ser Leu Asn Ala Asp Ala Val Arg Thr Pro His Glu Asp Ala Ser
                165                 170                 175

Glu Leu Trp Asp Ala Val Thr Asn Gly Asp Arg Thr Ala Ser Gly Ile
            180                 185                 190

Ala His Val Trp Leu Asp Gly Val Arg Arg Ala Ala Leu Asp Thr Ser
    195                 200                 205

Val Gly Gln Ile Gly Ala Pro Lys Ala Trp Ser Ala Gly Tyr Asp Gly
    210                 215                 220

Lys Gly Val Lys Ile Ala Val Leu Asp Thr Gly Val Asp Thr Ser His
225                 230                 235                 240

Pro Asp Leu Lys Gly Arg Val Thr Ala Ser Lys Asn Phe Thr Ala Ala
                245                 250                 255

Pro Gly Ala Gly Asp Lys Val Gly His Gly Thr His Val Ala Ser Ile
                260                 265                 270

Ala Ala Gly Thr Gly Ala Gln Ser Lys Gly Lys Tyr Lys Gly Val Ala
    275                 280                 285

Pro Gly Ala Ala Ile Leu Asn Gly Lys Val Leu Asp Asp Ser Gly Phe
    290                 295                 300

Gly Asp Asp Ser Gly Ile Leu Ala Gly Met Glu Trp Ala Ala Ala Gln
305                 310                 315                 320

Gly Ala Asp Val Val Asn Met Ser Leu Gly Gly Met Asp Thr Pro Glu
                325                 330                 335

Thr Asp Pro Leu Glu Ala Ala Val Asp Lys Leu Ser Ala Glu Lys Gly
            340                 345                 350

Val Leu Phe Ala Ile Ala Ala Gly Asn Glu Gly Pro Glu Ser Ile Gly
    355                 360                 365

Ser Pro Gly Ser Ala Asp Ala Leu Thr Val Gly Ala Val Asp Asp
    370                 375                 380

Lys Asp Lys Leu Ala Asp Phe Ser Ser Thr Gly Pro Arg Leu Gly Asp
385                 390                 395                 400

Gly Ala Ile Lys Pro Asp Val Thr Ala Pro Gly Val Asp Ile Thr Ala
```

```
                    405                 410                 415
Ala Ser Ala Glu Gly Asn Asp Ile Gly Gln Glu Val Gly Glu Gly Pro
                420                 425                 430

Ala Gly Tyr Met Thr Ile Ser Gly Thr Ser Met Ala Thr Pro His Val
            435                 440                 445

Ala Gly Ala Ala Ala Leu Leu Lys Gln Gln His Pro Asp Trp Thr Ser
450                 455                 460

Ala Glu Leu Lys Gly Ala Leu Thr Gly Ser Thr Lys Gly Gly Lys Tyr
465                 470                 475                 480

Thr Pro Phe Glu Gln Gly Ser Gly Arg Ile Gln Ala Asp Lys Ala Leu
                485                 490                 495

Gln Gln Thr Val Ile Ala Asp Pro Val Ser Val Ser Phe Gly Val Gln
            500                 505                 510

Gln Trp Pro His Thr Asp Asp Glu Pro Val Thr Lys Gln Leu Thr Tyr
        515                 520                 525

Arg Asn Leu Gly Thr Gln Asp Val Thr Leu Lys Leu Thr Ser Thr Ala
530                 535                 540

Thr Asp Pro Lys Gly Lys Ala Pro Ala Gly Phe Phe Thr Leu Gly
545                 550                 555                 560

Ala Thr Thr Val Thr Val Pro Ala Gly Gly Ser Ala Ser Val Asp Met
                565                 570                 575

Thr Ala Asp Thr Arg Leu Gly Gly Thr Val Asp Gly Ala Tyr Ser Ala
            580                 585                 590

Tyr Val Val Ala Thr Gly Gly Gly Gln Thr Val Arg Thr Ala Ala Ala
        595                 600                 605

Val Gln Arg Glu Val Glu Ser Tyr Asp Val Thr Val Arg His Ile Gly
610                 615                 620

Arg Asp Gly Lys Pro Thr Thr Glu His Leu Thr Asp Leu Ile Gly Tyr
625                 630                 635                 640

Ala Gly Leu Gly Ser Gly Arg Gly Tyr Gly Ala Pro Ala Thr Asp Thr
                645                 650                 655

Ala Thr Leu Arg Leu Pro Lys Gly Thr Tyr Leu Val Asp Ser Trp Ile
            660                 665                 670

Ala Lys Asp Phe Gly Thr Leu Lys Gly Gly Ile Asp Trp Leu Val Gln
        675                 680                 685

Pro Lys Leu Ser Val Thr Lys Asp Thr Thr Leu Thr Leu Asp Ala Arg
690                 695                 700

Thr Thr Lys Ala Ala Asp Ile Thr Val Pro Asp Pro Lys Ala Lys Pro
705                 710                 715                 720

Leu Ser Ala Thr Ile Gly Tyr Tyr Asp Thr Ala Gly Ile
                725                 730                 734

(2) INFORMATION FOR SEQ ID NO:5:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (iv) ANTI-SENSE: yes (v) FRAGMENT TYPE: internal fragment (xi) SEQUENCE DESCRIPTION: SEQ ID NO:5:

CCG TGG CGG TGG AGC CAC TCC AGC CGG TCG GCC TCG CCG GAC AGG TCG      48
Pro Trp Arg Trp Ser His Ser Ser Arg Ser Ala Ser Pro Asp Arg Ser
```

```
    1               5                      10                       15
AAG GCG GAG TTC TCG GGG GCG CGG GGG GCG ATC TTC GCG TAG                   90
Lys Ala Glu Phe Ser Gly Ala Arg Gly Ala Ile Phe Ala
                20                      25              29
```

(2) INFORMATION FOR SEQ ID NO:6:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (iv) ANTI-SENSE: yes (v) FRAGMENT TYPE: internal fragment (xi) SEQUENCE DESCRIPTION: SEQ ID NO:6:

```
CGG CGC GCC TTG AGC CTG GCG AAC AGT TCG GCT GGC GCG AGC CCC TGA           48
Arg Arg Ala Leu Ser Leu Ala Asn Ser Ser Ala Gly Ala Ser Pro
 1               5                      10                  15
```

(2) INFORMATION FOR SEQ ID NO:7:

(i) SEQUENCE CHARACTERISTICS:
        (A) LENGTH: 520 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Leu Asp Thr Ser Val Gly Gln Ile Gly Ala Pro Lys Ala Trp Ser Ala
 1               5                      10                  15

Gly Tyr Asp Gly Lys Gly Val Lys Ile Ala Val Leu Asp Thr Gly Val
                20                  25                  30

Asp Thr Ser His Pro Asp Leu Lys Gly Arg Val Thr Ala Ser Lys Asn
            35                  40                  45

Phe Thr Ala Ala Pro Gly Ala Gly Asp Lys Val Gly His Gly Thr His
    50                  55                  60

Val Ala Ser Ile Ala Ala Gly Thr Gly Ala Gln Ser Lys Gly Lys Tyr
65                  70                  75                  80

Lys Gly Val Ala Pro Gly Ala Ala Ile Leu Asn Gly Lys Val Leu Asp
                85                  90                  95

Asp Ser Gly Phe Gly Asp Asp Ser Gly Ile Leu Ala Gly Met Glu Trp
            100                 105                 110

Ala Ala Ala Gln Gly Ala Asp Val Val Asn Met Ser Leu Gly Gly Met
        115                 120                 125

Asp Thr Pro Glu Thr Asp Pro Leu Glu Ala Ala Val Asp Lys Leu Ser
    130                 135                 140

Ala Glu Lys Gly Val Leu Phe Ala Ile Ala Ala Gly Asn Glu Gly Pro
145                 150                 155                 160

Glu Ser Ile Gly Ser Pro Gly Ser Ala Asp Ala Ala Leu Thr Val Gly
                165                 170                 175

Ala Val Asp Asp Lys Asp Lys Leu Ala Asp Phe Ser Ser Thr Gly Pro
            180                 185                 190

Arg Leu Gly Asp Gly Ala Ile Lys Pro Asp Val Thr Ala Pro Gly Val
        195                 200                 205

Asp Ile Thr Ala Ala Ser Ala Glu Gly Asn Asp Ile Gly Gln Glu Val
    210                 215                 220
```

-continued

```
Gly Glu Gly Pro Ala Gly Tyr Met Thr Ile Ser Gly Thr Ser Met Ala
225                 230                 235                 240

Thr Pro His Val Ala Gly Ala Ala Ala Leu Leu Lys Gln Gln His Pro
            245                 250                 255

Asp Trp Thr Ser Ala Glu Leu Lys Gly Ala Leu Thr Gly Ser Thr Lys
                260                 265                 270

Gly Gly Lys Tyr Thr Pro Phe Glu Gln Gly Ser Gly Arg Ile Gln Ala
        275                 280                 285

Asp Lys Ala Leu Gln Gln Thr Val Ile Ala Asp Pro Val Ser Val Ser
        290                 295                 300

Phe Gly Val Gln Gln Trp Pro His Thr Asp Asp Glu Pro Val Thr Lys
305                 310                 315                 320

Gln Leu Thr Tyr Arg Asn Leu Gly Thr Gln Asp Val Thr Leu Lys Leu
                325                 330                 335

Thr Ser Thr Ala Thr Asp Pro Lys Gly Lys Ala Ala Pro Ala Gly Phe
                340                 345                 350

Phe Thr Leu Gly Ala Thr Thr Val Thr Val Pro Ala Gly Gly Ser Ala
            355                 360                 365

Ser Val Asp Met Thr Ala Asp Thr Arg Leu Gly Gly Thr Val Asp Gly
    370                 375                 380

Ala Tyr Ser Ala Tyr Val Val Ala Thr Gly Gly Gln Thr Val Arg
385                 390                 395                 400

Thr Ala Ala Val Gln Arg Glu Val Glu Ser Tyr Asp Val Thr Val
                405                 410                 415

Arg His Ile Gly Arg Asp Gly Lys Pro Thr Thr Glu His Leu Thr Asp
            420                 425                 430

Leu Ile Gly Tyr Ala Gly Leu Gly Ser Gly Arg Gly Tyr Gly Ala Pro
        435                 440                 445

Ala Thr Asp Thr Ala Thr Leu Arg Leu Pro Lys Gly Thr Tyr Leu Val
    450                 455                 460

Asp Ser Trp Ile Ala Lys Asp Phe Gly Thr Leu Lys Gly Gly Ile Asp
465                 475                 480

Trp Leu Val Gln Pro Lys Leu Ser Val Thr Lys Asp Thr Thr Leu Thr
                485                 490                 495

Leu Asp Ala Arg Thr Thr Lys Ala Ala Asp Ile Thr Val Pro Asp Pro
            500                 505                 510

Lys Ala Lys Pro Leu Ser Ala Thr
            515                 520
```